United States Patent
Kusens

(10) Patent No.: US 10,342,478 B2
(45) Date of Patent: Jul. 9, 2019

(54) METHOD AND SYSTEM FOR DETERMINING WHETHER A CARETAKER TAKES APPROPRIATE MEASURES TO PREVENT PATIENT BEDSORES

(71) Applicant: CERNER INNOVATION, INC., Kansas City, KS (US)

(72) Inventor: Neil Kusens, Sherman Oaks, CA (US)

(73) Assignee: Cerner Innovation, Inc., Kansas City, KS (US)

( * ) Notice: Subject to any disclaimer, the term of this patent is extended or adjusted under 35 U.S.C. 154(b) by 166 days.

(21) Appl. No.: 15/148,151

(22) Filed: May 6, 2016

(65) Prior Publication Data
US 2016/0324460 A1   Nov. 10, 2016

Related U.S. Application Data

(60) Provisional application No. 62/158,248, filed on May 7, 2015.

(51) Int. Cl.
  *A61B 5/00* (2006.01)
  *A61B 5/11* (2006.01)

(52) U.S. Cl.
  CPC .......... *A61B 5/447* (2013.01); *A61B 5/1113* (2013.01); *A61B 5/1128* (2013.01); *A61B 5/1116* (2013.01); *A61B 5/746* (2013.01)

(58) Field of Classification Search
  CPC ......... A61B 5/11; A61B 5/112; A61B 5/1113; A61B 5/1115; A61B 5/447; A61B 5/746; A61B 5/1128; G06K 9/00208; H04N 7/183; H04N 13/0203
  See application file for complete search history.

(56) References Cited

U.S. PATENT DOCUMENTS

| | | |
|---|---|---|
| 4,669,263 A | 6/1987 | Sugiyama |
| 4,857,716 A | 8/1989 | Gombrich et al. |
| 5,031,228 A | 7/1991 | Lu |
| 5,276,432 A | 1/1994 | Travis |
| 5,448,221 A | 9/1995 | Weller |
| 5,482,050 A | 1/1996 | Smokoff et al. |
| 5,592,153 A | 1/1997 | Welling et al. |

(Continued)

FOREIGN PATENT DOCUMENTS

| | | |
|---|---|---|
| DE | 19844918 A1 | 4/2000 |
| WO | 2007/081629 A2 | 7/2007 |

(Continued)

OTHER PUBLICATIONS

US 9,948,899 B1, 04/2018, Kusens (withdrawn)

(Continued)

*Primary Examiner* — Max F Hindenburg
(74) *Attorney, Agent, or Firm* — Shook, Hardy & Bacon L.L.P.

(57) ABSTRACT

Systems and methods for reducing the chance that a patient will develop a bedsore may determine whether a caregiver physically approaches a patient and remains in close physical proximity to a patient for a time sufficient to perform a bedsore prevention action. If a planned bedsore prevention action does not appear to be performed, the systems and methods may alert the patient, the caregiver, or others. A determination may be made as to whether the patient's position has changed in a manner consistent with a bedsore prevention action.

20 Claims, 10 Drawing Sheets

(56) References Cited

U.S. PATENT DOCUMENTS

| | | |
|---|---|---|
| 5,798,798 A | 8/1998 | Rector et al. |
| 5,838,223 A | 11/1998 | Gallant et al. |
| 5,915,379 A | 6/1999 | Wallace et al. |
| 5,942,986 A | 8/1999 | Shabot et al. |
| 6,050,940 A | 4/2000 | Braun et al. |
| 6,095,984 A | 8/2000 | Amano et al. |
| 6,160,478 A | 12/2000 | Jacobsen et al. |
| 6,174,283 B1 | 1/2001 | Nevo et al. |
| 6,188,407 B1 | 2/2001 | Smith et al. |
| 6,269,812 B1 | 8/2001 | Wallace et al. |
| 6,287,452 B1 | 9/2001 | Allen et al. |
| 6,322,502 B1 | 11/2001 | Schoenberg et al. |
| 6,369,838 B1 | 4/2002 | Wallace et al. |
| 6,429,869 B1 | 8/2002 | Kamakura et al. |
| 6,614,349 B1 | 9/2003 | Proctor et al. |
| 6,727,818 B1 | 4/2004 | Wildman et al. |
| 6,804,656 B1 | 10/2004 | Rosenfeld et al. |
| 7,015,816 B2 | 3/2006 | Wildman et al. |
| 7,122,005 B2 | 10/2006 | Shusterman |
| 7,154,397 B2 | 12/2006 | Zerhusen et al. |
| 7,237,287 B2 | 7/2007 | Weismiller et al. |
| 7,323,991 B1 | 1/2008 | Eckert et al. |
| 7,408,470 B2 | 8/2008 | Wildman et al. |
| 7,420,472 B2 | 9/2008 | Tran |
| 7,430,608 B2 | 9/2008 | Noonan et al. |
| 7,502,498 B2 | 3/2009 | Wen et al. |
| 7,612,679 B1 | 11/2009 | Fackler et al. |
| 7,669,263 B2 | 3/2010 | Menkedick et al. |
| 7,715,387 B2 | 5/2010 | Schuman |
| 7,724,147 B2 | 5/2010 | Brown |
| 7,756,723 B2 | 7/2010 | Rosow et al. |
| 7,890,349 B2 | 2/2011 | Cole et al. |
| 7,893,842 B2 | 2/2011 | Deutsch |
| 7,895,055 B2 | 2/2011 | Schneider et al. |
| 7,908,153 B2 | 3/2011 | Scherpbier et al. |
| 7,945,457 B2 | 5/2011 | Zaleski |
| 7,962,544 B2 | 6/2011 | Torok et al. |
| 7,972,140 B2 | 7/2011 | Renaud |
| 8,108,036 B2 | 1/2012 | Tran |
| 8,123,685 B2 | 2/2012 | Brauers et al. |
| 8,128,596 B2 | 3/2012 | Carter |
| 8,224,108 B2 | 7/2012 | Steinberg et al. |
| 8,237,558 B2 | 8/2012 | Seyed Momen et al. |
| 8,273,018 B1 | 9/2012 | Fackler et al. |
| 8,432,263 B2 | 4/2013 | Kunz |
| 8,451,314 B1 | 5/2013 | Cline et al. |
| 8,529,448 B2 | 9/2013 | McNair |
| 8,565,500 B2 | 10/2013 | Neff |
| 8,620,682 B2 | 12/2013 | Bechtel et al. |
| 8,655,680 B2 | 2/2014 | Bechtel et al. |
| 8,700,423 B2 | 4/2014 | Eaton, Jr. et al. |
| 8,727,981 B2 | 5/2014 | Bechtel et al. |
| 8,769,153 B2 | 7/2014 | Dziubinski |
| 8,890,937 B2 | 11/2014 | Skubic et al. |
| 8,902,068 B2 | 12/2014 | Bechtel et al. |
| 8,917,186 B1 | 12/2014 | Grant |
| 8,953,886 B2 | 2/2015 | King et al. |
| 9,072,929 B1 | 7/2015 | Rush et al. |
| 9,129,506 B1 | 9/2015 | Kusens |
| 9,147,334 B2 | 9/2015 | Long et al. |
| 9,159,215 B1 | 10/2015 | Kusens |
| 9,269,012 B2 | 2/2016 | Fotland |
| 9,292,089 B1 | 3/2016 | Sadek |
| 9,305,191 B2 | 4/2016 | Long et al. |
| 9,408,561 B2 | 8/2016 | Stone et al. |
| 9,424,699 B2 | 8/2016 | Kusens et al. |
| 9,466,163 B2 | 10/2016 | Kusens et al. |
| 9,489,820 B1 | 11/2016 | Kusens |
| 9,519,969 B1 | 12/2016 | Kusens |
| 9,524,443 B1 | 12/2016 | Kusens |
| 9,536,310 B1 | 1/2017 | Kusens |
| 9,538,158 B1 | 1/2017 | Rush et al. |
| 9,563,955 B1 | 2/2017 | Kamarshi et al. |
| 9,597,016 B2 | 3/2017 | Stone et al. |
| 9,691,206 B2 | 6/2017 | Kusens et al. |
| 9,729,833 B1 | 8/2017 | Kusens |
| 9,741,227 B1 | 8/2017 | Kusens |
| 9,774,991 B2 | 9/2017 | Kusens |
| 9,838,849 B2 | 12/2017 | Kusens |
| 9,858,741 B2 | 1/2018 | Kusens et al. |
| 9,892,310 B2 | 2/2018 | Kusens et al. |
| 9,892,311 B2 | 2/2018 | Kusens et al. |
| 9,892,611 B1 | 2/2018 | Kusens |
| 9,905,113 B2 | 2/2018 | Kusens |
| 9,984,521 B1 | 5/2018 | Kusens et al. |
| 9,997,001 B2 | 6/2018 | Kusens et al. |
| 9,998,857 B2 | 6/2018 | Kusens |
| 10,013,831 B1 | 7/2018 | Kusens et al. |
| 10,078,956 B1 | 9/2018 | Kusens |
| 10,090,068 B2 | 10/2018 | Kusens et al. |
| 10,091,463 B1 | 10/2018 | Kusens |
| 10,096,223 B1 | 10/2018 | Kusens |
| 10,109,179 B2 | 10/2018 | Kusens |
| 10,115,253 B2 | 10/2018 | Kusens et al. |
| 10,115,254 B1 | 10/2018 | Kusens et al. |
| 10,121,299 B2 | 11/2018 | Kusens et al. |
| 2002/0015034 A1 | 2/2002 | Malmborg |
| 2002/0038073 A1 | 3/2002 | August |
| 2002/0077863 A1 | 6/2002 | Rutledge et al. |
| 2002/0101349 A1 | 8/2002 | Rojas, Jr. |
| 2002/0115905 A1 | 8/2002 | August |
| 2002/0183976 A1 | 12/2002 | Pearce |
| 2003/0037786 A1 | 2/2003 | Biondi et al. |
| 2003/0070177 A1 | 4/2003 | Kondo et al. |
| 2003/0092974 A1 | 5/2003 | Santoso et al. |
| 2003/0095147 A1 | 5/2003 | Daw |
| 2003/0135390 A1 | 7/2003 | O'Brien et al. |
| 2003/0140928 A1 | 7/2003 | Bui et al. |
| 2003/0227386 A1 | 12/2003 | Pulkkinen et al. |
| 2004/0019900 A1 | 1/2004 | Knightbridge et al. |
| 2004/0052418 A1 | 3/2004 | DeLean |
| 2004/0054760 A1 | 3/2004 | Ewing et al. |
| 2004/0097227 A1 | 5/2004 | Siegel |
| 2004/0116804 A1 | 6/2004 | Mostafavi |
| 2004/0193449 A1 | 9/2004 | Wildman et al. |
| 2005/0038326 A1 | 2/2005 | Mathur |
| 2005/0182305 A1 | 8/2005 | Hendrich |
| 2005/0231341 A1 | 10/2005 | Shimizu |
| 2005/0249139 A1 | 11/2005 | Nesbit |
| 2006/0004606 A1 | 1/2006 | Wendl |
| 2006/0047538 A1 | 3/2006 | Condurso et al. |
| 2006/0049936 A1 | 3/2006 | Collins et al. |
| 2006/0058587 A1 | 3/2006 | Heimbrock et al. |
| 2006/0089541 A1 | 4/2006 | Braun et al. |
| 2006/0092043 A1 | 5/2006 | Lagassey |
| 2006/0107295 A1 | 5/2006 | Margis et al. |
| 2006/0145874 A1 | 7/2006 | Fredriksson et al. |
| 2006/0261974 A1 | 11/2006 | Albert et al. |
| 2007/0085690 A1 | 4/2007 | Tran |
| 2007/0118054 A1 | 5/2007 | Pinhas et al. |
| 2007/0120689 A1 | 5/2007 | Zerhusen et al. |
| 2007/0129983 A1 | 6/2007 | Scherpbier et al. |
| 2007/0136102 A1 | 6/2007 | Rodgers |
| 2007/0136218 A1 | 6/2007 | Bauer et al. |
| 2007/0159332 A1 | 7/2007 | Koblasz |
| 2007/0279219 A1 | 12/2007 | Warriner |
| 2007/0296600 A1 | 12/2007 | Dixon et al. |
| 2008/0001763 A1 | 1/2008 | Raja et al. |
| 2008/0002860 A1 | 1/2008 | Super et al. |
| 2008/0004904 A1 | 1/2008 | Tran |
| 2008/0009686 A1 | 1/2008 | Hendrich |
| 2008/0015903 A1 | 1/2008 | Rodgers |
| 2008/0071210 A1 | 3/2008 | Moubayed et al. |
| 2008/0087719 A1 | 4/2008 | Sahud |
| 2008/0106374 A1 | 5/2008 | Sharbaugh |
| 2008/0126132 A1 | 5/2008 | Warner et al. |
| 2008/0228045 A1 | 9/2008 | Gao et al. |
| 2008/0249376 A1 | 10/2008 | Zaleski |
| 2008/0267447 A1 | 10/2008 | Kelusky et al. |
| 2008/0277486 A1 | 11/2008 | Seem et al. |
| 2008/0281638 A1 | 11/2008 | Weatherly et al. |
| 2009/0082829 A1 | 3/2009 | Panken et al. |
| 2009/0091458 A1 | 4/2009 | Deutsch |
| 2009/0099480 A1 | 4/2009 | Salgo et al. |

(56) References Cited

U.S. PATENT DOCUMENTS

| | | |
|---|---|---|
| 2009/0112630 A1 | 4/2009 | Collins, Jr. et al. |
| 2009/0119843 A1 | 5/2009 | Rodgers et al. |
| 2009/0177327 A1 | 7/2009 | Turner et al. |
| 2009/0224924 A1 | 9/2009 | Thorp |
| 2009/0278934 A1 | 11/2009 | Ecker et al. |
| 2009/0322513 A1 | 12/2009 | Hwang et al. |
| 2010/0117836 A1 | 5/2010 | Seyed Momen et al. |
| 2010/0169114 A1 | 7/2010 | Henderson et al. |
| 2010/0169120 A1 | 7/2010 | Herbst et al. |
| 2010/0172567 A1 | 7/2010 | Prokoski |
| 2010/0176952 A1 | 7/2010 | Bajcsy et al. |
| 2010/0188228 A1 | 7/2010 | Hyland |
| 2010/0205771 A1 | 8/2010 | Pietryga et al. |
| 2010/0245577 A1 | 9/2010 | Yamamoto et al. |
| 2010/0285771 A1 | 11/2010 | Peabody |
| 2010/0305466 A1 | 12/2010 | Corn |
| 2011/0018709 A1 | 1/2011 | Kombluh |
| 2011/0022981 A1 | 1/2011 | Mahajan et al. |
| 2011/0025493 A1 | 2/2011 | Papadopoulos et al. |
| 2011/0025499 A1 | 2/2011 | Hoy et al. |
| 2011/0035057 A1 | 2/2011 | Receveur et al. |
| 2011/0035466 A1 | 2/2011 | Panigrahi |
| 2011/0054936 A1 | 3/2011 | Cowan et al. |
| 2011/0068930 A1 | 3/2011 | Wildman et al. |
| 2011/0077965 A1 | 3/2011 | Nolte et al. |
| 2011/0087079 A1 | 4/2011 | Aarts |
| 2011/0087125 A1 | 4/2011 | Causevic |
| 2011/0102133 A1 | 5/2011 | Shaffer |
| 2011/0102181 A1 | 5/2011 | Metz et al. |
| 2011/0106560 A1 | 5/2011 | Eaton, Jr. et al. |
| 2011/0106561 A1 | 5/2011 | Eaton, Jr. et al. |
| 2011/0175809 A1 | 7/2011 | Markovic et al. |
| 2011/0190593 A1 | 8/2011 | McNair |
| 2011/0227740 A1 | 9/2011 | Wohltjen |
| 2011/0254682 A1 | 10/2011 | Sigrist Christensen |
| 2011/0288811 A1 | 11/2011 | Greene |
| 2011/0295621 A1 | 12/2011 | Farooq et al. |
| 2011/0301440 A1 | 12/2011 | Riley et al. |
| 2011/0313325 A1 | 12/2011 | Cuddihy |
| 2012/0016295 A1 | 1/2012 | Tsoukalis |
| 2012/0025991 A1 | 2/2012 | O'Keefe et al. |
| 2012/0026308 A1 | 2/2012 | Johnson et al. |
| 2012/0075464 A1 | 3/2012 | Derenne et al. |
| 2012/0092162 A1 | 4/2012 | Rosenberg |
| 2012/0098918 A1 | 4/2012 | Murphy |
| 2012/0154582 A1 | 6/2012 | Johnson et al. |
| 2012/0212582 A1 | 8/2012 | Deutsch |
| 2012/0259650 A1 | 10/2012 | Mallon et al. |
| 2012/0314901 A1 | 12/2012 | Hanson et al. |
| 2012/0323090 A1 | 12/2012 | Bechtel et al. |
| 2012/0323591 A1 | 12/2012 | Bechtel et al. |
| 2012/0323592 A1 | 12/2012 | Bechtel et al. |
| 2013/0027199 A1 | 1/2013 | Bonner |
| 2013/0120120 A1 | 5/2013 | Long et al. |
| 2013/0122807 A1 | 5/2013 | Tenarvitz et al. |
| 2013/0127620 A1 | 5/2013 | Siebers et al. |
| 2013/0184592 A1 | 7/2013 | Venetianer et al. |
| 2013/0265482 A1 | 10/2013 | Funamoto |
| 2013/0309128 A1 | 11/2013 | Voegeli et al. |
| 2013/0332184 A1 | 12/2013 | Burnham et al. |
| 2014/0039351 A1 | 2/2014 | Mix et al. |
| 2014/0070950 A1 | 3/2014 | Snodgrass |
| 2014/0081654 A1 | 3/2014 | Bechtel et al. |
| 2014/0085501 A1 | 3/2014 | Tran |
| 2014/0086450 A1 | 3/2014 | Huang et al. |
| 2014/0108041 A1 | 4/2014 | Bechtel et al. |
| 2014/0155755 A1 | 6/2014 | Pinter et al. |
| 2014/0191861 A1 | 7/2014 | Scherrer |
| 2014/0213845 A1 | 7/2014 | Bechtel et al. |
| 2014/0267625 A1 | 9/2014 | Clark et al. |
| 2014/0327545 A1 | 11/2014 | Bolling et al. |
| 2014/0333744 A1 | 11/2014 | Baym et al. |
| 2014/0354436 A1 | 12/2014 | Nix et al. |
| 2014/0365242 A1 | 12/2014 | Neff |
| 2015/0057635 A1 | 2/2015 | Bechtel et al. |
| 2015/0109442 A1 | 4/2015 | Derenne et al. |
| 2015/0206415 A1 | 7/2015 | Wegelin et al. |
| 2015/0269318 A1 | 9/2015 | Neff |
| 2015/0278456 A1 | 10/2015 | Bermudez Rodriguez et al. |
| 2016/0022218 A1 | 1/2016 | Hayes et al. |
| 2016/0070869 A1 | 3/2016 | Portnoy |
| 2016/0093195 A1 | 3/2016 | Ophardt |
| 2016/0098676 A1 | 4/2016 | Kusens et al. |
| 2016/0127641 A1 | 5/2016 | Gove |
| 2016/0180668 A1 | 6/2016 | Kusens et al. |
| 2016/0183864 A1 | 6/2016 | Kusens et al. |
| 2016/0217347 A1 | 7/2016 | Mineo |
| 2016/0253802 A1 | 9/2016 | Venetianer et al. |
| 2016/0267327 A1 | 9/2016 | Franz et al. |
| 2016/0314258 A1 | 10/2016 | Kusens |
| 2017/0055917 A1 | 3/2017 | Stone et al. |
| 2017/0084158 A1 | 3/2017 | Kusens |
| 2017/0091562 A1 | 3/2017 | Kusens |
| 2017/0109991 A1 | 4/2017 | Kusens |
| 2017/0143240 A1 | 5/2017 | Stone et al. |
| 2017/0193177 A1 | 7/2017 | Kusens |
| 2017/0193279 A1 | 7/2017 | Kusens et al. |
| 2017/0193772 A1 | 7/2017 | Kusens et al. |
| 2017/0195637 A1 | 7/2017 | Kusens et al. |
| 2017/0289503 A1 | 10/2017 | Kusens |
| 2018/0068545 A1 | 3/2018 | Kusens |
| 2018/0104409 A1 | 4/2018 | Bechtel et al. |
| 2018/0114053 A1 | 4/2018 | Kusens et al. |
| 2018/0137340 A1 | 5/2018 | Kusens et al. |
| 2018/0144605 A1 | 5/2018 | Kusens |
| 2018/0189946 A1 | 7/2018 | Kusens et al. |
| 2018/0190098 A1 | 7/2018 | Kusens |

FOREIGN PATENT DOCUMENTS

| | | |
|---|---|---|
| WO | 2009018422 A1 | 2/2009 |
| WO | 2012122002 A1 | 9/2012 |
| WO | 2016/126845 A1 | 8/2016 |
| WO | 2017/058991 A1 | 4/2017 |
| WO | 2017/124056 A1 | 7/2017 |

OTHER PUBLICATIONS

Final Office Action dated Sep. 29, 2017 in U.S. Appl. No. 14/757,877, 22 pages.

Final Office Action dated Oct. 4, 2017 in U.S. Appl. No. 14/623,349, 30 pages.

Notice of Allowance dated Oct. 10, 2017 in U.S. Appl. No. 14/727,434, 9 pages.

Final Office Action dated Oct. 12, 2017 in U.S. Appl. No. 14/599,498, 28 pages.

Notice of Allowance dated Oct. 20, 2017 in U.S. Appl. No. 15/279,054, 14 pages.

First Action Interview Pre-Interview Communication dated Nov. 22, 2017 in U.S. Appl. No. 15/134,189, 4 pages.

Notice of Allowance dated Dec. 6, 2017 in U.S. Appl. No. 15/395,716, 5 pages.

Final Office Action dated Dec. 12, 2017 in U.S. Appl. No. 14/575,850, 10 pages.

Non-Final Office Action dated Sep. 23, 2016 in U.S. Appl. No. 14/727,434, 9 pages.

Non-Final Office Action dated May 8, 2017 in U.S. Appl. No. 15/395,250, 19 pages.

Notice Notice of Allowance dated Jul. 5, 2017 in U.S. Appl. No. 14/727,434, 9 pages.

Notice of Allowance dated Jul. 24, 2017 in U.S. Appl. No. 15/395,716, 5 pages.

Non-Final Office Action dated Aug. 16, 2017 in U.S. Appl. No. 14/757,593, 8 pages.

Final Office Action dated Aug. 23, 2017 in U.S. Appl. No. 15/285,416, 16 pages.

Notice of Allowance dated Sep. 21, 2017 in U.S. Appl. No. 15/395,526, 13 pages.

Notice of Allowance dated Sep. 26, 2017 in U.S. Appl. No. 15/395,250, 13 pages.

(56) References Cited

OTHER PUBLICATIONS

Tom Mooney, "Rhode Island ER first to test Google Glass on medical conditions", http://www.ems1.com/ems-products/cameras-video/articles/1860487-Rhode-Island-ER-first . . . printed on Mar. 11, 2014.
Pending U.S. Application by same inventor Neil Kusens, U.S. Appl. No. 14/575,850, filed Dec. 18, 2014, entitled "Method and Process for Determining Whether an Individual Suffers a Fall Requiring Assistance".
Pending U.S. Application by same inventor Neil Kusens, U.S. Appl. No. 14/611,363, filed Feb. 2, 2015, entitled "Method and System for Determining Whether an Individual Takes Appropriate Measures to Prevent the Spread of Healthcare Associated Infections".
Pending U.S. Application by same inventor Neil Kusens, U.S. Appl. No. 14/623,349, filed Feb. 16, 2015, entitled "Method for Determining Whether an Individual Enters a Prescribed Virtual Zone Using 3D Blob Detection".
Pending U.S. Application by same inventor Neil Kusens, U.S. Appl. No. 14/724,969, filed May 29, 2015, entitled "Method and Process for Determining Whether an Individual Suffers a Fall Requiring Assistance".
Pending U.S. Application by same inventor Neil Kusens, U.S. Appl. No. 14/727,434, filed Jun. 1, 2015, entitled "Method for Determining Whether Enters a Prescribed Virtual Zone Using Skeletal Tracking and 3D Blob Detection".
Pending U.S. Application by same inventor Neil Kusens, U.S. Appl. No. 14/728,762, filed Jun. 2, 2015, entitled "Method for Determining Whether an Individual Leaves a Prescribed Virtual Perimeter".
Pending U.S. Application by same inventor Neil Kusens, U.S. Appl. No. 14/599,498, filed Jan. 17, 2015, entitled "Method and System for Determining Whether an Individual Takes Appropriate Measures to Prevent the Spread of Healthcare Associated Infections".
Pending U.S. Application by same inventor Neil Kusens, U.S. Appl. No. 14/743,264, filed Jun. 18, 2015, entitled "System for Determining Whether an Individual Enters a Prescribed Virtual Zone Using 3D Blob Detection".
Pending U.S. Application by same inventor Neal Kusens. U.S. Appl. No. 14/611,363, filed Feb. 2, 2015, entitled "Method and System for Determining Whether an Individual Takes Appropriate Measures to Prevent the Spread of Healthcare Associated Infections".
Pending U.S. Application by same inventor Neal Kusens, U.S. Appl. No. 14/613,866, filed Feb. 4, 2015, entitled "Method and System for Determining Whether an Individual Takes Appropriate Measures to Prevent the Spread of Healthcare Associated Infections Along With Centralized Monitoring".
Non-Final Office Action dated Dec. 30, 2013 in U.S. Appl. No. 13/543,816, 9 pages.
Final Office Action dated Jun. 17, 2014 in U.S. Appl. No. 13/543,816, 15 pages.
Non-Final Office Action dated Dec. 1, 2014 in U.S. Appl. No. 13/543,816, 18 pages.
Non-Final Office Action dated Jul. 16, 2014 in U.S. Appl. No. 14/084,588, 12 pages.
Final Office Action dated Dec. 19, 2014 in U.S. Appl. No. 14/084,588, 24 pages.
Notice of Allowance dated Jun. 5, 2015 in U.S. Appl. No. 13/543,816, 5 pages.
Non-Final Office Action dated Oct. 7, 2015 in U.S. Appl. No. 14/339,397, 16 pages.
Non-Final Office Action dated Feb. 11, 2016 in U.S. Appl. No. 14/724,969, 14 pages.
Non-Final Office Action dated Mar. 11, 2016 in U.S. Appl. No. 14/575,850, 10 pages.
Non-Final Office Action dated May 23, 2016 in U.S. Appl. No. 14/743,499, 5 pages.
Notice of Allowance dated May 31, 2016 in U.S. Appl. No. 14/743,447, 8 pages.
Notice of Allowance dated Jun. 22, 2016 in U.S. Appl. No. 14/743,447, 4 pages.
Notice of Allowance dated Jun. 27, 2016 in U.S. Appl. No. 14/728,762, 14 pages.
Notice of Allowance dated Jul. 18, 2016 in U.S. Appl. No. 14/743,264, 16 pages.
Final Office Action dated Jul. 28, 2016 in U.S. Appl. No. 14/723,969, 26 pages.
Notice of Allowance dated Aug. 26, 2016 in U.S. Appl. No. 14/743,447, 5 pages.
Notice of Allowance dated Sep. 19, 2016 in U.S. Appl. No. 14/743,499, 5 pages.
Notice of Allowance dated Oct. 14, 2016 in U.S. Appl. No. 14/743,264, 14 pages.
Notice of Allowance dated Nov. 9, 2016 in U.S. Appl. No. 14/743,264, 14 pages.
Notice of Allowance dated Nov. 14, 2016 in U.S. Appl. No. 14/743,447, 5 pages.
Notice of Allowance dated Dec. 23, 2016 in U.S. Appl. No. 14/724,969, 5 pages.
Non-Final Office Action dated Jan. 11, 2017 in U.S. Appl. No. 14/611,363, 19 pages.
Non-Final Office Action dated Feb. 23, 2017 in U.S. Appl. No. 14/757,877, 24 pages.
First Action Interview Preinterview Communication dated Feb. 24, 2017 in U.S. Appl. No. 15/395,716, 5 pages.
Notice of Allowance dated Mar. 20, 2017 in U.S. Appl. No. 14/613,866, 11 pages.
Non-Final Office Action dated Apr. 5, 2017 in U.S. Appl. No. 14/623,349, 15 pages.
Non-Final Office Action dated Apr. 11, 2017 in U.S. Appl. No. 15/285,416, 13 pages.
Notice of Allowance dated Apr. 19, 2017 in U.S. Appl. No. 15/395,716, 5 pages.
Non-Final Office Action dated Apr. 21, 2017 in U.S. Appl. No. 14/757,593, 9 pages.
Notice of Allowance dated Apr. 21, 2017 in U.S. Appl. No. 14/724,969, 9 pages.
Notice of Allowance dated Apr. 25, 2017 in U.S. Appl. No. 14/727,434, 9 pages.
Final Office Action dated Apr. 28, 2017 in U.S. Appl. No. 14/757,593, 20 pages.
Non-Final Office Action dated May 31, 2017 in U.S. Appl. No. 14/599,498, 24 pages.
Notice of Allowance dated Dec. 29, 2017 in U.S. Appl. No. 14/611,363, 11 pages.
Notice of Allowance dated Feb. 12, 2018 in U.S. Appl. No. 14/623,349, 12 pages.
Final Office Action dated Feb. 16, 2018 in U.S. Appl. No. 14/757,593, 8 pages.
First Action Interview Office Action dated Feb. 22, 2018 in U.S. Appl. No. 15/134,189, 4 pages.
Non-Final Office Action dated Feb. 22, 2018 in U.S. Appl. No. 14/599,498, 24 pages.
Non-Final Office Action dated Mar. 14, 2018 in U.S. Appl. No. 14/757,877, 13 pages.
Non-Final Office Action dated May 31, 2018 in U.S. Appl. No. 15/39,762, 24 pages.
Non-Final Office Action dated May 31, 2018 in U.S. Appl. No. 15/848,621, 23 pages.
Notice of Allowance dated Jun. 4, 2018 in U.S. Appl. No. 14/757,593, 5 pages.
Non-Final Office Action dated Jun. 8, 2018 in U.S. Appl. No. 15/628,318, 9 new pages.
Notice of Allowance dated Jun. 13, 2018 in U.S. Appl. No. 14/575,850, 5 pages.
Notice of Allowance dated Jun. 18, 2018 in U.S. Appl. No. 14/623,349, 11 pages.
Notice of Allowance dated Jun. 19, 2018 in U.S. Appl. No. 15/395,716, 2 pages.
Final Office Action dated Jul. 5, 2018 in U.S. Appl. No. 15/285,416, 8 pages.
Final Office Action dated Jul. 12, 2018 in U.S. Appl. No. 15/134,189, 23 pages.

(56) References Cited

OTHER PUBLICATIONS

Notice of Allowance dated Jul. 13, 2018 in U.S. Appl. No. 15/396,263, 9 pages.
Notice of Allowance dated Jul. 18, 2018 in U.S. Appl. No. 14/599,498, 6 pages.
Notice of Allowance dated Jul. 23, 2018 in U.S. Appl. No. 15/728,110, 15 pages.
Non-Final Office Action dated Aug. 15, 2018 in U.S. Appl. No. 15/910,632, 7 pages.
Raheja, et al., "Human Facial Expression Detection From Detected in CapturedImage Using Back Propagation Neural Network", International Journal of Computer Science and Information Technology (IJCSIT), vol. 2, No. 1, Feb. 2010, 8 pages.
Final Office Action dated Oct. 18, 2017 in U.S. Appl. No. 15/396,263, 20 pages.
First Action Interview Office Action dated Nov. 28, 2017 in U.S. Appl. No. 14/244,160, 3 pages.
Non-Final Office Action dated Apr. 14, 2017 in U.S. Appl. No. 15/396,263, 18 pages.
Notice of Allowance dated Nov. 27, 2017 in U.S. Appl. No. 15/279,054, 2 pages.
First Action Interview Pre-Interview Communication dated May 21, 2018 in U.S. Appl. No. 15/910,645, 14 pages.
Non-Final Office Action dated Feb. 7, 2018 in U.S. Appl. No. 15/396,263, 19 pages.
Non-Final Office Action dated Mar. 12, 2018 in U.S. Appl. No. 15/285,416, 20 pages.
Non-Final Office Action dated May 2, 2018 in U.S. Appl. No. 15/728,110, 8 pages.
Non-Final Office Action dated May 7, 2018 in U.S. Appl. No. 14/611,363, 6 pages.
Notice of Allowance dated Jan. 18, 2018 in U.S. Appl. No. 15/279,054, 2 pages.
Notice of Allowance dated May 9, 2018 in U.S. Appl. No. 15/395,716, 5 pages.
Non Final Office Action received for U.S. Appl. No. 15/395,243, dated Feb. 14, 2019, 14 pages.
Non Final Office Action received for U.S. Appl. No. 16/216,210, dated Feb. 13, 2019, 29 pages.
Non Final Office Action received for U.S. Appl. No. 16/107,567, dated Mar. 29, 2019, 8 pages.

METHOD AND SYSTEM FOR DETERMINING WHETHER A CARETAKER TAKES APPROPRIATE MEASURES TO PREVENT PATIENT BEDSORES

CROSS-REFERENCE TO RELATED APPLICATIONS

This application claims the benefit of U.S. Provisional Application No. 62/158,248, filed on May 7, 2015, which is hereby incorporated by reference in its entirety.

TECHNICAL FIELD

This disclosure relates generally to computerized methods and systems for determining whether a caretaker takes appropriate measure to prevent patient bedsores.

BACKGROUND

Bedsores, also called pressure sores or pressure ulcers, are skin and tissue injuries from prolonged pressure applied to the skin. Bedsores most commonly develop on the skin covering bony parts of the body, such as hips, heels, and ankles. Bedsores are a significant threat to patients with a medical condition which limits their ability to change position, such as a patient confined to a bed for an extended period of time. These bedsores can develop quickly and become a severe health issue requiring costly treatment. The medical facility must typically bear the cost of bedsores, which puts a strain on the finances of the healthcare provider. It is typically far less expensive to prevent bedsores than it is to treat bedsores that have developed.

Bedsores are prevented by having the patient change positions frequently in order to avoid pressure and stress being placed on vulnerable areas for extended time periods. These position changes should take place about every two hours, although each treatment plan is unique to the patient.

BRIEF SUMMARY

This brief summary is meant to present an overview of concepts related to this disclosure, and is expressly not meant to define or identify key elements of the disclosure in isolation from the remainder of the disclosure, including the figures.

This disclosure generally relates to systems, methods, and media for monitoring whether a caregiver has taken appropriate steps to prevent or mitigate patient bedsores. The systems and methods may be computerized and, once configured, may operate without human engagement or intervention unless or until an alarm condition arises.

In some aspects, this disclosure relates to a method of reducing the chance that a patient will develop a bedsore. The method may comprise receiving, from a wireless receiver associated with one of a caregiver and a patient, data regarding a signal strength for a signal received from a wireless transmitter associated with the other of the caregiver and the patient. The method may comprise determining, by a computerized monitoring system, when the signal strength indicates that the caregiver has approached the patient. The method may comprise determining, by the computerized monitoring system, and using the data regarding the strength of the signal from the wireless receiver, whether the caregiver enters a virtual patient or bed zone around the patient within a specified period of time for performing a bedsore prevention action, and whether the caregiver remains within the virtual patient or bed zone around the patient for a predetermined period of time sufficient to perform one or more bedsore prevention actions.

The method may comprise issuing, by a computerized communication system in electronic communication with the computerized monitoring system, an alert when the caregiver has not approached the virtual patient or bed zone around the patient within the specified period of time for performing a bedsore prevention action or has not remained within the virtual patient or bed zone around the patient for the predetermined period of time sufficient to perform one or more bedsore prevention actions. The alert may be directed to the patient, the caregiver, an alternate caregiver, a centralized monitoring station, or a combination thereof. The method may further comprise receiving, by the computerized monitoring system, data from a 3D motion sensor co-located with the patient. The method may further comprise determining, by the computerized monitoring system and based on the data from the 3D motion sensor, whether the patient has changed position consistent with a bedsore prevention action within the specified time for performing the bedsore prevention action. The method may further comprise issuing, by a computerized communication system in electronic communication with the computerized monitoring system, an alert when the patient has not sufficiently changed position to comply with a bedsore prevention action within the specified period of time for performing a bedsore prevention action.

The method may comprise displaying images from a 3D motion sensor on a centralized monitoring station primary display. The method may comprise displaying images from the 3D motion sensor on a centralized monitoring station alert display upon receipt of an alert. The method may comprise identifying a caregiver that has entered the virtual patient zone or virtual bed zone around the patient, by the computerized monitoring system, based on data received from the wireless transmitter. The method may comprise using data from a 3D motion sensor co-located with the patient to confirm the identity of a caregiver that has entered the virtual patient or bed zone. The method may comprise recording in a database whether the caregiver enters the virtual patient or bed zone around the patient within the specified period of time for performing a bedsore prevention action, and whether the caregiver remains within the virtual patient or bed zone around the patient for the predetermined period of time sufficient to perform one or more bedsore prevention actions.

In some aspects, this disclosure relates to a system for reducing the chance that a patient will develop a bedsore. The system may comprise a wireless transmitter associated with one of a caregiver and a patient. The system may comprise a wireless receiver associated with the other of the caregiver and the patient. The wireless receiver may be configured to receive transmissions from the wireless transmitter when the wireless transmitter is within range of the wireless receiver. The system may comprise a computerized monitoring system configured to receive signal strength data from the wireless receiver when the wireless receiver is within range of the wireless transmitter. The computerized monitoring system may be configured to determine whether a caregiver has entered a virtual patient or bed zone within a specified period of time and has remained within the virtual patient or bed zone around the patient for a predetermined period of time sufficient to perform one or more bedsore prevention actions. The system may comprise a computerized communication system configured to receive an alert from the computerized monitoring system upon a determination that a caregiver has not entered a virtual patient or bed zone within the specified period of time or has not remained within the virtual patient or bed zone around the patient for the predetermined period of time sufficient to perform one or more bedsore prevention actions. The computerized communication system may be configured to communicate an alert to at least one of the patient, the caregiver, an alternate caregiver, a database, and a centralized monitoring station.

The system may comprise a 3D motion sensor. The computerized monitoring system may be configured to receive image data from the 3D motion sensor. The centralized monitoring station may comprise a primary display. Image data from a 3D motion sensor may be displayed on the primary display. The centralized monitoring station may comprise a second display area. The second display area may be configured to display image data from the 3D motion sensor upon receipt of an alert that the caregiver has not entered the virtual patient or bed zone within the specified period of time or has not remained within the virtual patient or bed zone around the patient for the predetermined period of time sufficient to perform one or more bedsore prevention actions. The computerized communication system may be configured to communicate an alert to the patient, the caregiver, the alternate caregiver, or another human user using one or more of an amplifying speaker, a public announcement system, a television, a monitor, a mobile phone, a computer, a pager, a system for varying lighting conditions, an automated phone call, a voice mail message, an e-mail message, an SMS message, and a video.

The computerized monitoring system may be configured to determine, using data from a 3D motion sensor, whether the patient has changed position consistent with a bedsore prevention action within the specified time for performing the bedsore prevention action. The computerized monitoring system may be configured to determine whether the patient has changed position consistent with a bedsore prevention action within the specified time for performing the bedsore prevention action after determining that the caregiver has entered and remained within the virtual patient or bed zone around the patient within the specified time for performing the bedsore prevention action and for the predetermined period of time sufficient to perform the bedsore prevention action.

In some aspects, this disclosure relates to computer storage media embodying computer-executable instructions. The computer storage media may exclude signals per se. The computer-executable instructions may be instructions for performing a method for reducing the chance that a patient will develop a bedsore. The instructions may comprise an action after determining that the caregiver has entered and remained within the virtual patient or bed zone around the patient within the specified time for performing the bedsore prevention action and for the predetermined period of time sufficient to perform the bedsore prevention action. The instructions may comprise a virtual zone module configured to define a virtual zone around a patient. The instructions may comprise an action determination module configured to analyze data from the wireless receiver and determine whether a caregiver enters the virtual zone within a specified period of time for performing a bedsore prevention action, and whether the caregiver remains within the virtual patient or bed zone around the patient for a predetermined period of time sufficient to perform one or more bedsore prevention actions. The instructions may comprise a communication module configured to send one or more alerts upon determining that the caregiver has not entered the virtual zone within the specified period of time for performing the bedsore prevention action, or the caregiver has not remained within the virtual patient or bed zone around the patient for the predetermined period of time sufficient to perform one or more bedsore prevention actions.

The claimed solution is necessarily rooted in computerized electronic technology in order to supplement human-effectuated processes, providing information that would otherwise be unavailable to a human caregiver (e.g., observing a patient's change in position when the caregiver is not with the patient) and/or has evaded a human caregiver (e.g., due to forgetfulness or distractions). If adhering to the routine, conventional execution of a bedsore prevention regimen, a caregiver would perform unnecessary repositioning operations when unaware that a patient had self-repositioned in the caregiver's absence. A caregiver unable to perform a bedsore prevention action according to a designated schedule, if delayed due to unavoidable tasks such as urgent attendance to other matters, might similarly be unable to interrupt the immediate task to request assistance from an alternate or back-up caregiver. The systems, methods, and processes claimed do not replace, but rather supplement and improve on, routine and conventional bedsore prevention regimens.

The claimed invention overcomes the limitations of current computer healthcare information technology, which may, at best, accept user input to document the completion of a bedsore prevention action, and provides other benefits that will become clear to those skilled in the art from the following description.

The claimed systems, methods and media represent a new paradigm of facilitating compliance with a bedsore prevention plan, and/or determining whether a caregiver has taken measures to prevent patient bedsores. Not only does the claimed invention easily document bedsore prevention actions without manual data entry, but it also prevents errors and delays in completing bedsore prevention actions. Users of electronic medical records or electronic health records utilizing the claimed invention will notice fewer user steps to utilize the EMR in conjunction with a bedsore prevention plan and user access to the data regarding the bedsore prevention plan and/or compliance with the bedsore prevention plan. Furthermore, anything that reduces the number of "clicks" or entries a computer or mobile device user has to make in an EMR or EHR to record bedsore prevention actions results in reducing the memory utilization, CPU cycles, number of operations that need to be performed by the computer, and power consumption, as well as eliminating the task of data recordation for the caregiver. The resulting cost savings and operational efficiencies of a computer electronic medical record magnify the potential benefits of this technology.

Additional objects, advantages, and novel features of this disclosure will be set forth in part in the description which follows, and in part will become apparent to those skilled in the art upon examination of the following, or may be learned by practice of this disclosure.

BRIEF DESCRIPTION OF THE SEVERAL VIEWS OF THE DRAWING

This disclosure references the attached drawing figures, wherein.

DETAILED DESCRIPTION

Figure 1:
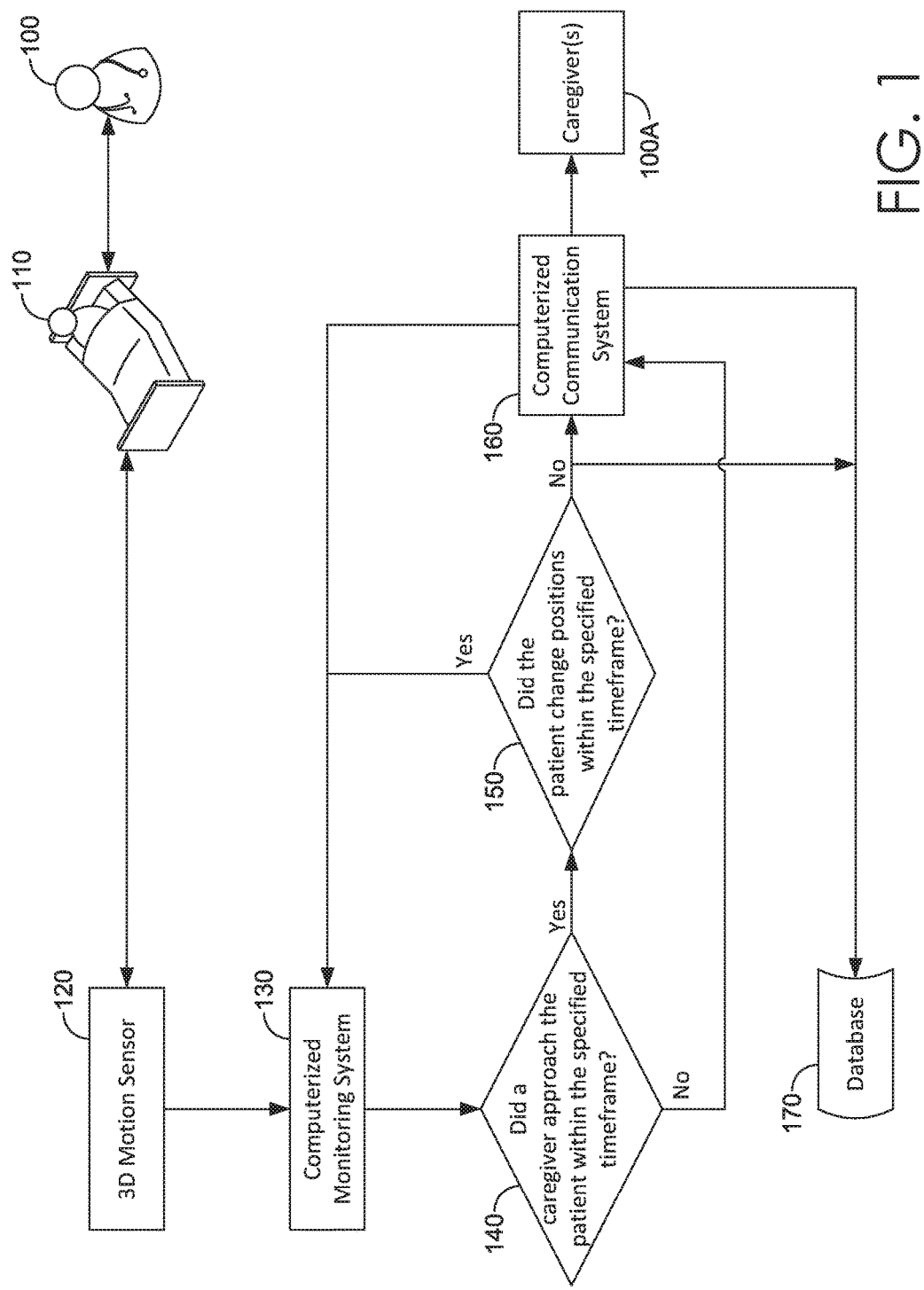
FIG. 1 is a schematic overview of an exemplary system and method for reducing the chance that a patient will develop a bedsore, in accordance with aspects of this disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As used in this disclosure, a "patient" refers to a person at risk of bedsores, without regard to whether that person is under the immediate care of a medical professional, e.g., in a hospital, clinic, surgical center, outpatient diagnostic center, outpatient treatment center, rehabilitation facility, hospice care facility, assisted living facility, group home, private home, or other environment. As used in this disclosure, a "caregiver" or "caretaker" may be a clinician, such as a doctor, nurse, physician's assistant, nurse's aide, orderly, physical therapist, and the like, or may be a paid or unpaid assistant who helps the patient with health care and/or tasks of daily living, such as a visiting nurse, a home health aide, a paid companion, a relative, a friend, or the like.

Bedsores are not typically a problem for strong, healthy people. Before a pressure sore forms, a healthy person will become uncomfortable and will shift position, alleviating the pressure on the spot where the discomfort occurred. However, individuals experiencing limited mobility, loss of consciousness, loss of sensation, or other conditions may not perceive the need to move after sitting or lying in a particular position for an extended time, or may lack the ability to reposition themselves to alleviate the pressure on a particular body part. Chronic conditions pose an apparent risk of bedsores, but even acute conditions may put a person at risk of bedsores during the period of illness or injury and recuperation.

Whether being cared for in a medical facility or in a home or home-like facility, a patient may be placed on a bedsore prevention plan or regimen, specifying certain bedsore prevention actions to be undertaken on a schedule. Typical bedsore prevention actions include changing the position of the patient on a regular basis, such as every 2 hours. These actions are more effective when they are undertaken as part of a consistent regimen. However, even diligent caregivers may find it difficult to consistently comply with a bedsore prevention regimen, especially when the bedsore prevention regimen remains in place for an extended or indefinite period of time. Rolling or repositioning a patient repetitively over days, weeks, or years, may make it difficult to remember when the patient was last repositioned, for example, 2 hours ago or 4 hours ago. Professional caregivers may have other patients to tend to, and may find themselves unavailable to reposition a particular patient at a particular time because of the urgent needs of a different patient. Lay caregivers may also care for multiple patients, or may be distracted by other responsibilities, such as children or other employment. A caregiver may enter a patient's room with the intention to reposition the patient and become distracted by other, more immediate needs of the patient. Of course, like anyone else, a caregiver may simply lose track of time between scheduled bedsore prevention actions.

The methods, systems, and computer-readable media disclosed herein provide for automated, computerized systems that can help reduce the chance that a patient will develop a bedsore. The methods, systems, and media can monitor a caregiver's proximity to the patient, assessing whether a caregiver gets close enough to the patient for a sufficiently long time to have performed one or more bedsore prevention actions. Alternately, or additionally, the methods, systems, and media may assess whether a patient's position has changed sufficiently that the change in position is likely to serve the purpose of a bedsore prevention action, regardless of whether the patient is repositioned by a caregiver or self-repositions. If a predetermined period of time, such as a time specified in a patient's bedsore prevention regimen, elapses without detection of a change in position or a close-proximity interaction with the caregiver for a suitable duration, the system may alert the patient, the caregiver, or others. These alerts may improve compliance with a bedsore prevention regimen, and, therefore, reduce the chance that the patient will develop a bedsore. It will be appreciated by those of skill in the art that a bedsore prevention regimen may be used with patients with existing bedsores, and that the same or similar bedsore prevention actions may also facilitate healing of existing bedsores and/or prevent exacerbating existing bedsores.

An exemplary method and system for reducing the chance that a patient will develop a bedsore are shown in FIG. 1. A 3D motion sensor 120 may be co-located with patient 110, who is tended by caregiver 100. For example, 3D motion sensor 120 may be located in or near a hospital room, bedroom, or other location where patient 110 spends a significant amount of time. The 3D motion sensor 120 may be positioned to have a view of most or all of the patient's body.

In general, the 3D motion sensor 120 is an electronic device that contains one or more cameras capable of identifying individual objects, people, and motion, regardless of lighting conditions. The 3D motion sensor 120 may further comprise one or more microphones to detect audio. As used in this disclosure, unless expressly described otherwise, reference to a sensor or sensors encompasses the singular and the plural, e.g., a singular sensor or an array of sensors, and an array of sensors may be physically housed in a unitary structure or may be physically distinct devices. The cameras may utilize technologies including, but not limited to, color RGB, CMOS sensors, infrared projectors, RF-modulated light, Time of Flight (ToF, including LIDAR), and combinations thereof. The 3D motion sensor may further contain one or more microprocessors and/or image sensors to detect and process information sent and/or received by the one or more cameras. Suitable 3D motion sensors can perceive depth, in contrast to 2D cameras which perceive only lateral and longitudinal positions. Exemplary 3D motion sensors include the Microsoft® Kinect® Camera, the Sony® Playstation® Camera, and the Intel® RealSense® Camera, each of which happens to include one or more microphones, although many aspects of the disclosure can be practiced without sensing audio.

The 3D motion sensor 120 may be in electronic communication with a computerized monitoring system 130, either as a separate component of the same physical unit or device, or as separate devices. The 3D motion sensor 120 may be co-located with or remote from computerized monitoring system 130, so long as data can be sent by the 3D motion sensor 120 to the computer monitoring system 130 or retrieved by the computerized monitoring system 130 from the 3D motion sensor 120.

The 3D motion sensor 120 may operate continuously, or intermittently (for example, running for a fixed period at defined intervals), or on a trigger (e.g., when a motion detector or light sensor is activated, suggesting activity in the room). The 3D motion sensor 120 may operate continuously at all times while the monitoring is occurring, regardless of whether the person or object of interest is moving or not. The 3D motion sensor 120 may view the entire room or a large portion of the room by placement in a manner sufficient for the room to be visible to the camera. Alternately, the 3D motion sensor 120 may view any portion of the room that includes the patient or a portion of the patient to be monitored. The 3D motion sensor 120 may record video. Video is a series of sequential, individual picture frames (e.g., 30 frames per second of video). The video data may include 3D depth data and/or skeletal and/or blob or object tracking data. In some implementations, it may be desirable for the sensors to capture video only, or sound only, or video and sound. Video only (with 3D depth and/or skeletal and/or blob or object tracking data) may make monitored patients more comfortable having conversations with visitors or caregivers than if sound is also captured. Alternatively, or additionally, to protect patient privacy and modesty, video displays of the image data from the 3D motion sensor may be blurred or pixelated or otherwise obscured, or the people and objects in the room may be converted from detailed image data to cartoons, less detailed drawings, or stick figures when displayed. The 3D motion sensor may collect and transmit data sufficient for measuring and analyzing movement and interaction between different people within the room, but transmit only sufficient image data for a partially obscured video, or a microprocessor associated with the 3D motion sensor and/or computerized monitoring station may process image and/or video data to make the individuals and/or details of the room or the activity of the room more difficult to distinctly identify. In some aspects, only 3D depth data and/or skeletal and/or blob or object tracking data is transmitted, without video or still images.

The computerized monitoring system 130 may receive and analyze data from 3D motion sensor 120. The computerized monitoring system 130 and/or the 3D motion sensor 120 may be configured to monitor and/or analyze only a portion of the full view of the 3D motion sensor 120. For example, 3D motion sensor might be capable of viewing most or all of a room, or a room and part of an adjacent hallway. However, to reduce processing capacity and communication bandwidth requirements, the 3D motion sensor 120 may be configured to capture data from a limited view, and/or the computerized monitoring system 130 may be configured to analyze only a portion of the data from 3D motion sensor 120. For example, the computerized monitoring system 130 may analyze data from a pre-defined area around a patient, or around a patient's bed or chair. Exemplary processes for configuring the system in this manner are described below.

Computerized monitoring system 130 is specifically designed and programmed to monitor activity based on information received from 3D motion sensor 120. Computerized monitoring system 130 may use facial recognition, height, distance between body points, and/or other biometrics (e.g., iris scanning, fingerprints, etc.) to "lock onto" the patient for analysis, helping to avoid the possibility of the computerized monitoring system 130 tracking a visitor or caregiver who might pass between the patient and the 3D motion sensor, or others who may enter the 3D motion sensor's field of view. Computerized monitoring system 130 may use facial recognition, height, distance between body points, etc. to identify one or more caregivers for the patient, distinct from the features of the patient. Alternately, or in addition, 3D motion sensors and/or additional sensors, such as an RFID reader, may read an electronic receiver, transmitter, or transceiver associated with the patient and/or with a caregiver to identify and/or distinguish individuals in the room. The patient and/or the caregiver may wear, carry, or otherwise be associated with such a transceiver in the form of a badge, token, bracelet, cell phone, or other device. As one example, the patient may wear, carry, or otherwise be associated with a transmitter and the caregiver may wear, carry, or otherwise be associated with a receiver. Alternatively, the patient may wear, carry, or otherwise be associated with a receiver and the caregiver may wear, carry, or otherwise be associated with a transmitter. Or both the patient and the caregiver may wear, carry, or otherwise be associated with a transmitter or a receiver or both. This is described in greater detail below, with reference to FIG. 3.

Alternately, or additionally, the patient, the caregiver, or both may be associated with a bar code, words, QR code, or other visual symbol or identifier, for example, on an ID badge or bracelet. The 3D motion sensor 120 and/or the computerized monitoring system 130 may note the barcode, words, QR code, or other visual symbol or identifier, which could later be compared to a database to identify the patient or caregiver, or the 3D motion sensor 120 and/or the computerized monitoring system 130 could be given access to a database and configured to determine the identity of the patient and/or caregiver using the visual symbol or identifier. A person may be inferred to be a caregiver by identification of clothing such as scrubs, a hospital uniform, a lab coat, etc., in contrast to a hospital gown, nightgown, or street clothes. Similarly, a person in a hospital gown or nightgown may be inferred to be the patient. In a home or home-like environment, street clothes may be associated with the caregiver, while in a hospital or institutional environment, street clothes may be associated with a visitor.

The computerized monitoring system 130 may analyze data from 3D motion sensor 120 to determine whether a caregiver approached the patient within a specified timeframe, shown as step 140 in FIG. 1. The computerized monitoring system 130 may identify a particular caregiver, such as a particular clinician (e.g., Nurse Smith) or a particular family member (e.g., son Joe), as by use of facial recognition and/or use of a unique transmitter, receiver, or other electronic or visual identifier associated with the individual. Alternately, the computerized monitoring system 130 may distinguish between the patient and another person presumed to be a caregiver, without individually identifying the patient and/or the caregiver. As non-limiting examples, the computerized monitoring system 130 may detect a caregiver and patient by their clothing, or, if using skeletal recognition, may determine that two skeletons are present in the room, and determine a distance between the caregiver and the patient.

The computerized monitoring system 130 may determine whether the caregiver approaches the patient within a specified distance, the distance being small enough to suggest a physical interaction between the caregiver and the patient. The computerized monitoring system 130 may alternately use a virtual zone, configured around the patient and/or around the patient's bed or sitting area, and may assess whether the caregiver has entered the virtual zone. The configuration of the virtual zone is described below, with reference to FIGS. 4-9. The computerized monitoring system 130 may use a timer and analysis of data from 3D motion sensor 120 to determine whether the caregiver (or any caregiver or other person) has approached the patient with a specified period for performing a bedsore prevention action. For example, if the patient is on a bedsore prevention plan that requires repositioning the patient every two hours, and no caregiver approaches the patient for more than 2 hours, it can be inferred that the patient has not been assisted with repositioning. If the patient is not able to self-reposition, it can be inferred that the patient has not completed the scheduled bedsore prevention action.

It will be appreciated that the specified time period for performing a bedsore prevention action may be more or less than 2 hours, based on the policy of the caregiver or institution where the patient resides, the condition of the patient, the patient's relative risk of developing bedsores, or other clinical or non-clinical reasons. Different intervals may be used at different points in a 24-hour day, for example, allowing for longer intervals at night to permit the patient to sleep. The specified time period for performing the bedsore prevention action, as used in the methods and systems disclosed, may be somewhat less than that in the bedsore prevention plan. For example, if a bedsore prevention plan calls for a patient to be repositioned every 2 hours, the specified time period for determining whether a bedsore prevention action has been performed might be 1.5 hours, or 1.75 hours. In this way, an alert can be issued while there is still potentially time to reposition the patient in compliance with the bedsore prevention plan. Alternately, or additionally, the specified time period for determining whether a bedsore prevention action has been performed might be somewhat longer than the nominal plan intervals, for example, if a caregiver or institution considers it acceptable to comply with the planned action times within a certain tolerance, such as plus-or-minus 15 minutes, or plus-or-minus 30 minutes, it may be unnecessary to issue an alert until the nominal interval in the bedsore prevention plan has elapsed. In general, the specified time period may be based on, but is not necessarily equal to, the interval between bedsore prevention actions in the patient's bedsore prevention plan. Of course, the specified time period might also be equal to the interval between bedsore prevention actions in the patient's bedsore prevention plan.

If no caregiver approaches the patient within the specified time period for completing a bedsore prevention action, the computerized monitoring system 130 may send an alert to computerized communication system 160. Alternately, or additionally, the computerized monitoring system 130 may assess whether the patient has changed position consistent with a bedsore prevention activity within the specified time period for completing a bedsore prevention action, shown as step 150 in FIG. 1. Checking for a change in patient position may prevent at least some unnecessary alarms in situations where the patient was able to self-reposition within the specified time period. A confirmation notification may be sent, using methods and modes as for sending an alarm, that the patient has changed position. A confirmation notification avoids the caregiver unnecessarily going to the patient's room to perform bedsore prevention actions when the patient has self-repositioned consistent with a bedsore prevention action. Checking for a change in patient position may be omitted, for example, for an individual patient or for a type of patient who is known to be unable to self-reposition.

To assess the patient's position, computerized monitoring system 130 may use skeletal tracking, blob tracking, or other image recognition techniques to identify one or more tracking points on the patient's body, such as hips, shoulders, knees, chin, nose, etc. The patient's position can then be analyzed by tracking skeletal segments, or the shape and orientation of a blob, or specified tracking points. For example, the system may identify or infer the position of the patient's right knee at a time designated as T1, as by the coordinates (x1, y1, z1) of the patient's right knee in a picture frame. At a later time T2, the patient's right knee might be at coordinates (x2, y2, z2). Based on this information, motion, speed and direction of movement (or lack of movement) can be derived utilizing the elapsed time and comparing the two 3D coordinates. As opposed to conventional motion sensors, which use captured motion to control a camera, the 3D motion sensor used in the methods and systems described herein is used to compute the motion. Further, a 3D motion sensor, as opposed to a 2D motion sensor, offers depth sensitivity that can help to reduce false alarms (e.g., by identifying rotational or vertical movement, as might occur when a patient rolls to or from one side of the body), as well as help to isolate the analysis to the patient and avoid false alarms or false confirmations of repositioning from other objects or individuals who might pass in front of or behind the patient.

A minimum degree of change may be specified as a threshold for the computerized monitoring system 130 to determine that a patient has changed position. The degree of change may be specified in distance (e.g., the patient's right hip must move at least 9 cm before concluding that the patient has changed positions), or angular movement, or a combination thereof. It should be appreciated that in this regard, changing position refers to a movement or repositioning consistent with a bedsore prevention action. Not all movement will be a change in position in this regard. A patient may change position by moving or self-repositioning, by being moved or repositioned, by changing or shifting position, or by being rolled, rotated, shifted, or otherwise repositioned consistent with bedsore prevention actions.

If a caregiver has not approached the patient and/or the patient has not self-repositioned consistent with a bedsore prevention action, computerized monitoring system 130 may send an alert to computerized communication system 160. Computerized communication system 160 may send a human-intelligible signal for communicating a change in status (e.g., compliant with bedsore prevention plan to non-compliant with bedsore prevention plan, or vice versa) or request for attention.

For example, computerized communication system 160 may send an alert to an amplifying speaker, public announcement system, television, monitor, mobile phone, computer, pager, or other display device in a patient's room. The alert, which could be audible or visible or both, may request that the patient roll over or remind the patient that it is time to change position. The alert could be text, sound, or video, or could consist of flashing lights in the room or on a display, or another visible change in the patient's room, such as a change in the color of a border of a monitor or television, or a change in the brightness or color of the light in the room. The alert could take the form of an automated phone call, voice mail message, e-mail message, SMS message, or the like. Alerts to the patient may be disabled, for example, if the patient is unable to self-reposition without assistance.

In addition to or instead of alerting the patient, computerized communication system 160 may alert one or more caregivers 100A. As with alerts intended for a patient, alerts for a caregiver could be audible or visible or both, and may include text alerts, instructions, or other signals that something is amiss, e.g., flashing lights, color schemes, etc. An alert for a caregiver may be sent to the patient's room, or may be sent to a device carried by the caregiver, such as a cell phone or pager, or may be sent to a nursing station or dispatch center. An alert for a caregiver may be sent to a primary caregiver, and, if no change is detected within a predetermined response time, an alert may be sent to one or more additional caregivers. Alternately, an alert may be sent to two or more caregivers at the outset. Alerts may also be sent to others who might not have primary responsibility for the care of the patient, such as family members or guardians. Alerts, possibly including the 3D motion sensor data in the time period before the alert and/or any response(s) to the alert, may be recorded, for example, in database 170. Database 170 may include, or may provide information to, or may be accessible by, an Electronic Health Record (EHR) for one or more patients. In this way, routine alerts, responses, and/or completed bedsore prevention actions may be recorded automatically in an EHR without caregiver input. Exemplary responses to an alert may include a system determination that the patient has changed position consistent with a bedsore prevention action since the alert, or a human operator cancellation of the alert (e.g., based on a caregiver or centralized monitoring station attendant confirmation that the patient has changed position or for some reason should not change position at this time).

A confirmation that a bedsore prevention action was completed, either timely or after an alert, may be communicated to a patient, a caregiver, and/or others in any of the modes and manners described for alerts. A confirmation that a bedsore prevention action was completed may also be recorded in database 170, an EHR, or in any other desired file or storage location.

Figure 2:
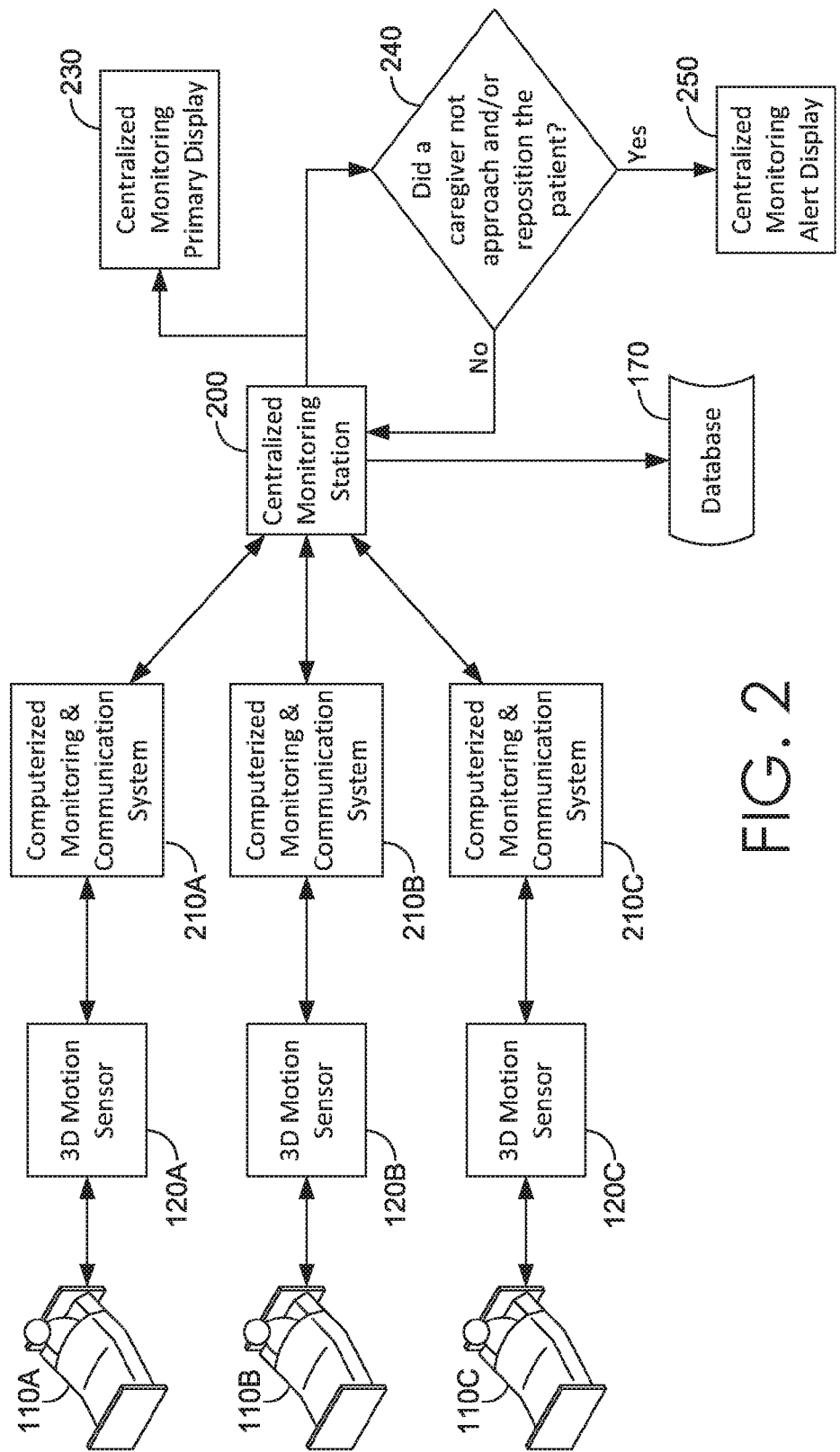
FIG. 2 is a schematic overview of an exemplary system and method for centralized monitoring, in accordance with aspects of this disclosure.

Computerized monitoring system 130 and/or computerized communication system 160, shown in FIG. 2 as combined computerized monitoring and communication systems 210A, 210B, and 210C, may also be in communication with a centralized monitoring station 200. A centralized monitoring station 200 may be used with a single 3D motion sensor 120 for a single patient. For example, centralized monitoring station 200 may include a display in a home of a family member or guardian of patient 110. As shown in FIG. 2, a plurality of 3D motion sensors 120A, 120B, and 120C may monitor a plurality of patients, 110A, 110B, and 110C, respectively. The 3D motion sensors 120A, 120B, and 120C may be monitored by distinct computerized monitoring and communication systems 210A, 210B, and 210C, respectively. Alternately, 3D motion sensors 120A, 120B, and 120C could each send 3D motion and/or sound data to a single computerized monitoring system 130 or to a single combined computerized monitoring and communication system.

The computerized monitoring system 130 and/or computerized monitoring and communication systems 210A, 210B, and 210C may send filtered or unfiltered data, such as images and/or a live video feed, with or without sound, from 3D motion sensors 120A, 120B, and 120C to centralized monitoring station 200. The 3D motion sensor data may be received and displayed on a centralized monitoring primary display 230, which may be a single display monitor or a series or grid of two or more display monitors. As mentioned above, the computerized monitoring system and/or the centralized monitoring station may apply filters before the 3D motion sensor data is displayed, for example, to blur or pixelate the face or body of the patient, to protect patient privacy. In addition, video and/or sound, if sound is provided, can be turned off at any node, including centralized monitoring primary display 230 and directly at the 3D motion sensor, to protect patient privacy, e.g., while the patient is receiving visitors, bathing, changing clothes, etc. If a large number of patients are being monitored at the same time, the centralized monitoring primary display 230 may be enlarged so that it can aggregate multiple telemetry feeds, or more than one centralized monitoring station primary display 230 could be used. Regardless of whether the data is filtered or unfiltered, it may still be processed by the computerized monitoring system 130, a computerized monitoring and communication system (e.g., 210A, 210B, or 210C) and/or the centralized monitoring station 200 to render the data as a human-intelligible visual image or series of images (e.g., video).

When the computerized communication system receives an alert, the computerized communication system may send the alert to the centralized monitoring station 200. At step 240, on receipt of a determination from the computerized monitoring system 130 and/or an alert from the computerized communication system 160 for a particular 3D motion sensor, the display from that sensor may be moved from centralized monitoring station primary display 230 to centralized monitoring station alert display 250 or duplicated on centralized monitoring station alert display 250. Centralized monitoring station alert display 250 may be a subset of the display or displays of centralized monitoring station primary display 230, or may be a distinct display or series of displays. If live video is available but is not being displayed on centralized monitoring station primary display 230, the live video may be displayed on centralized monitoring station alert display 250 after an alert is received. Centralized monitoring station alert display 250, or an attendant there, may analyze the video feed to determine what is happening in the patient's room. If a caregiver has arrived and is repositioning the patient, the centralized monitoring station alert display 250 or an attendant may clear the alert. If an alert has been sent to a caregiver and no response is detected or received, centralized monitoring station alert display 250 or an attendant may notify an alternate or back-up caregiver that the patient needs assistance with repositioning. Alerts and any actions taken or responses received or observed at centralized monitoring station 200 may be recorded, for example, to database 170.

The centralized monitoring station primary display 230 may routinely display live video for monitored patients. An attendant at the centralized monitoring station primary display 230 can use the live video feed to detect other problems, such as a patient fall, a patient gesture that he or she needs assistance, an unauthorized person has entered the patient's room, etc.

The various system components and/or method steps may be situated and/or performed remotely from one another. So long as the components can transfer data and perform the functions described, the components or any subcombination of components could be located together, even, in some aspects, in a singular physical housing. Alternately, the components or any subcombination of components could be remote from one another, either in different rooms, different floors of a building, different buildings, different cities, or even different countries or continents. The centralized monitoring station 200, for example, may reside at a nursing station on the same floor or on a different floor of the same building as the 3D motion sensor, or could be in a regional center that receives telemetry from a plurality of 3D motion sensors in different rooms, buildings, or even cities, and possibly in a variety of patient environments. That is, a computerized monitoring system, computerized communication system and/or centralized monitoring station may process data from 3D motion sensors in hospitals, outpatient centers, assisted living facilities, and/or private homes, or may be specific, e.g., to a particular patient or healthcare organization (such as a hospital or hospital network).

Figure 3:
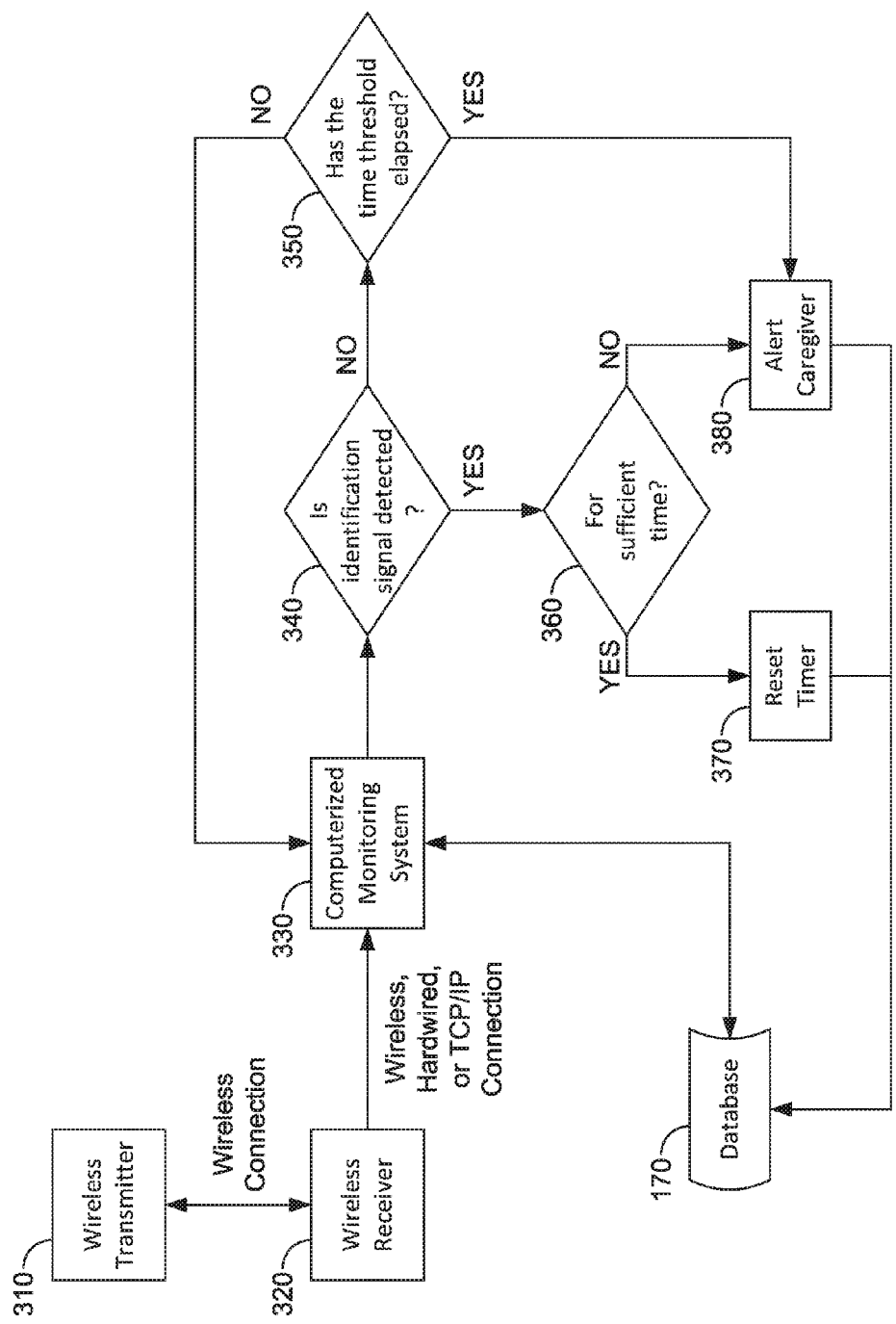
FIG. 3 is a schematic overview of an exemplary system and method for determining whether a caregiver takes appropriate measures to prevent patient bedsores, in accordance with aspects of this disclosure.

FIG. 3 shows an exemplary flowchart for determining whether a caregiver takes appropriate measures to prevent patient bedsores. The method and system of FIG. 3 represent an embodiment which uses a wireless transmitter and a wireless receiver, instead of or in addition to image or motion data analysis, to determine whether a bedsore prevention action was likely completed or not completed. As shown in FIG. 3, a wireless transmitter 310 and a wireless receiver 320 are used. The wireless transmitter 310 may be associated with the patient or an object near the patient, such as the patient's bed, or within a virtual patient zone and/or a virtual bed zone, as described below, and the wireless receiver 320 may be worn by the caregiver. Alternately, the wireless transmitter 310 may be associated with the caregiver, and the wireless receiver 320 associated with the patient. The wireless transmitter 310 may continuously broadcast a signal, possibly a signal unique to a particular individual, such as a particular patient or a particular caregiver. The broadcast or transmission may use, for example, Bluetooth, or any other long- or short-range frequency transmission technology. When in range, the wireless receiver 320 may measure the signal strength from the wireless transmitter 310, and transmit data regarding the signal strength to computerized monitoring system 330. The data may be transmitted using, for example, a wireless, hardwired, or TCP/IP connection between the wireless receiver 320 and the computerized monitoring system 330.

Computerized monitoring system 330 (which may be the same as computerized monitoring system 130, if image analysis is also being used) may use the signal to identify the caregiver and/or the patient, if a unique signal is associated with an individual caregiver and/or patient. Alternately, or additionally, computerized monitoring system 330 may infer an approximate distance between the wireless transmitter 310 and the wireless receiver 320 using the signal strength data. If the signal strength is below a predetermined threshold, computerized monitoring system 330 infers that the caregiver is not with the patient in a sense relevant to bedsore prevention actions, shown as step 340. For example, the caregiver may be in the patient's room, or in a nearby room or hallway, but not close enough to the patient to reposition the patient. If no caregiver signal is detected above the threshold level before a specified time for completing a bedsore prevention action elapses, the computerized monitoring system may send an alert to a computerized communication system 160 and/or a database 170. If no caregiver signal is detected and visual image analysis is also being used, computerized monitoring system 330 may go to step 150 in FIG. 1 to evaluate whether the patient has self-repositioned in the compliance window.

If the signal strength is above a predetermined threshold, this indicates that the caregiver is likely close enough to the patient to perform a bedsore prevention action. It may also be possible to select or configure the wireless transmitter and/or receiver so that the wireless receiver will only be in range to receive transmissions if the receiver and transmitter are sufficiently, physically close for it to be possible for a caregiver to perform a bedsore prevent action for the patient. If a caregiver signal identification is detected at step 340, computerized monitoring system 330 starts a proximity timer to measure how long the caregiver remains close enough to the patient to complete a bedsore prevention action, based on the signal strength reported by the wireless receiver 320. A predetermined time may be used as a minimum for assessing whether the caregiver might reasonably have completed a bedsore prevention action. The time may be a default for all patients, such as 1-3 minutes, or may be customized for the type of patient or for a particular patient. For example, it may take less time to safely and comfortably turn a small pediatric patient than a bariatric patient or a patient with a low pain tolerance. If the caregiver remained within the threshold proximity to the patient for the predetermined time, a timer for intervals between bedsore prevention actions may be reset, shown as step 370, for the next scheduled bedsore prevention action. If the caregiver does not remain within the threshold proximity to the patient for the predetermined time for completing a bedsore prevention action, computerized monitoring system 330 may issue one or more alerts to a computerized communication system and/or a database, as described above. As described above, confirmations of completed bedsore prevention activities may also be issued, and any desired data regarding the completion of a bedsore prevention action and/or alerts related to a bedsore prevention action can be stored in database 170 or an alternate file or storage location.

The timer and timer reset steps may also be employed when the caregiver's proximity is assessed from image data rather than from signal strength data from wireless receiver 320. Further, if a 3D motion sensor is used in conjunction with wireless transmitter 310 and wireless receiver 320, image analysis may be used to confirm the identity of the person wearing wireless transmitter 310 and/or wireless receiver 320. This identity confirmation may prevent confusion as to the identity of the patient and/or the caregiver, either by intentionally or inadvertently using another person's transmitter or receiver. For example, facial recognition algorithms could be used to compare the patient in the image data from 3D motion sensor 120 to a database entry (e.g., a photograph on file) for the patient associated with a particular transmitter or receiver, to confirm the patient's identification before recording data for that patient (e.g., in database 170 and/or an EHR for the patient). Alternately, or additionally, facial recognition algorithms could be used to compare the caregiver in the image data from 3D motion sensor 120 to a database entry (e.g., a photograph on file) to confirm the identity of the caregiver. This helps to ensure that any documentation generated by the computerized system is accurate, and that alerts are directed to appropriate people and devices.

Figure 4:
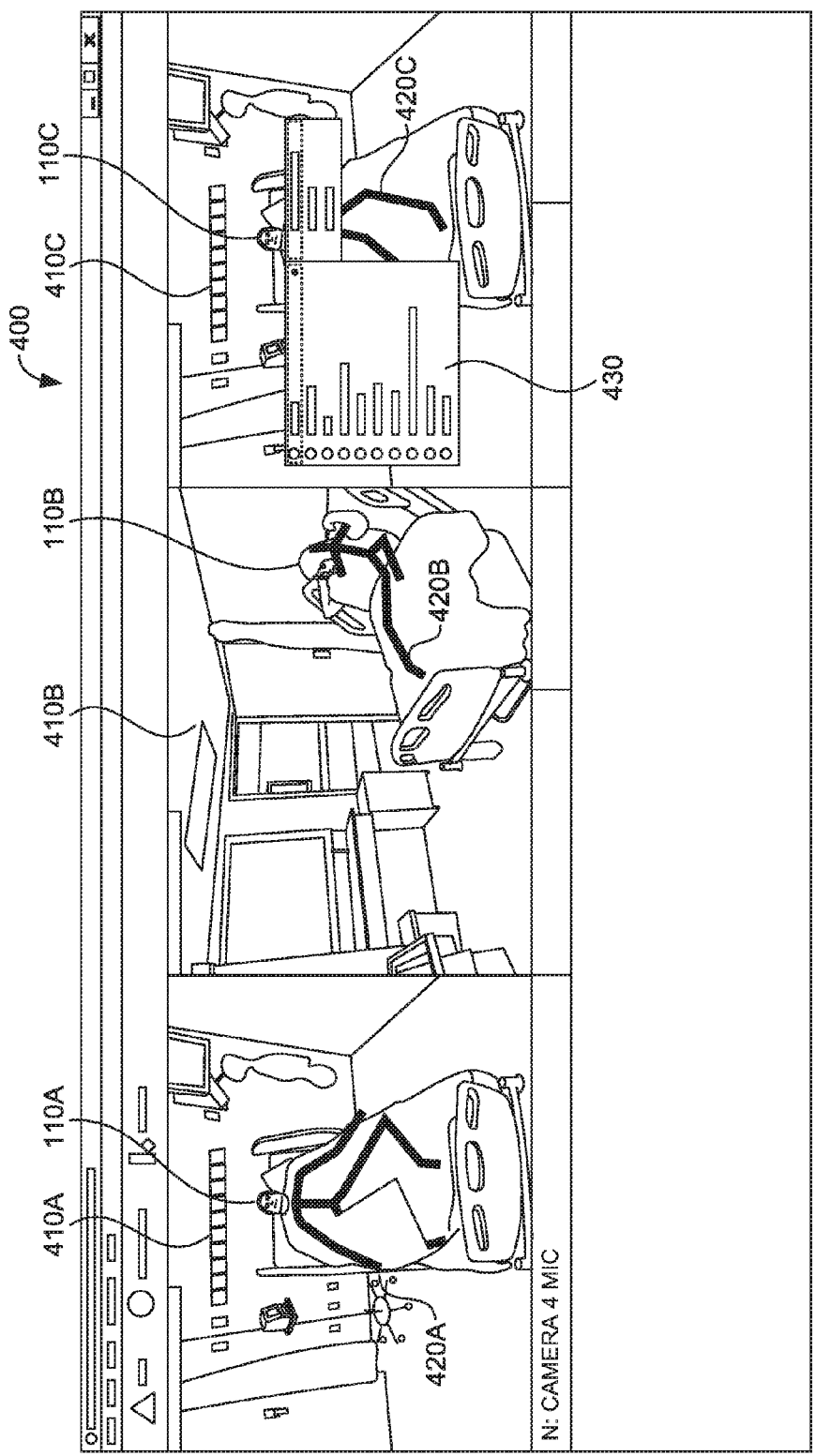
FIG. 4 is a view of an exemplary centralized monitoring primary display, in accordance with aspects of this disclosure.

As mentioned previously, the computerized monitoring system and/or centralized monitoring station may allow a user to configure a specific monitoring area around a patient or a location where the patient spends time, such as a bed, chair, chaise, etc. Such configuration is described, for example, in U.S. application Ser. No. 14/613,866, filed Feb. 4, 2015, which is hereby incorporated by reference in its entirety. FIG. 4 shows an exemplary display 400 of visual telemetry data for multiple patients 110A, 110B, and 110C, in simultaneous views 410A, 410B, and 410C, respectively, as might be configured on centralized monitoring station primary display 230. As shown, views 410A, 410B, and 410C appear on a split screen, however, different views could also be shown on separate displays. In addition to showing patients 110A, 110B, and 110C, display 400 shows skeleton FIGS. 420A, 420B, and 420C for each patient. It will be appreciated that although FIGS. 4-9 show a skeleton figure, any suitable means of tracking the patient's body position could be used, including, without limitation, blob tracking, object tracking, or other image recognition techniques to identify one or more specific tracking points on the patient's body, such as the patients hip(s), shoulder(s), knee(s), chin, nose, etc. In addition, view 410C shows a pop-up menu 430, which may present configuration options for view 410C or options for responding to an alarm associated with monitored patient 110C or both.

Figure 5:
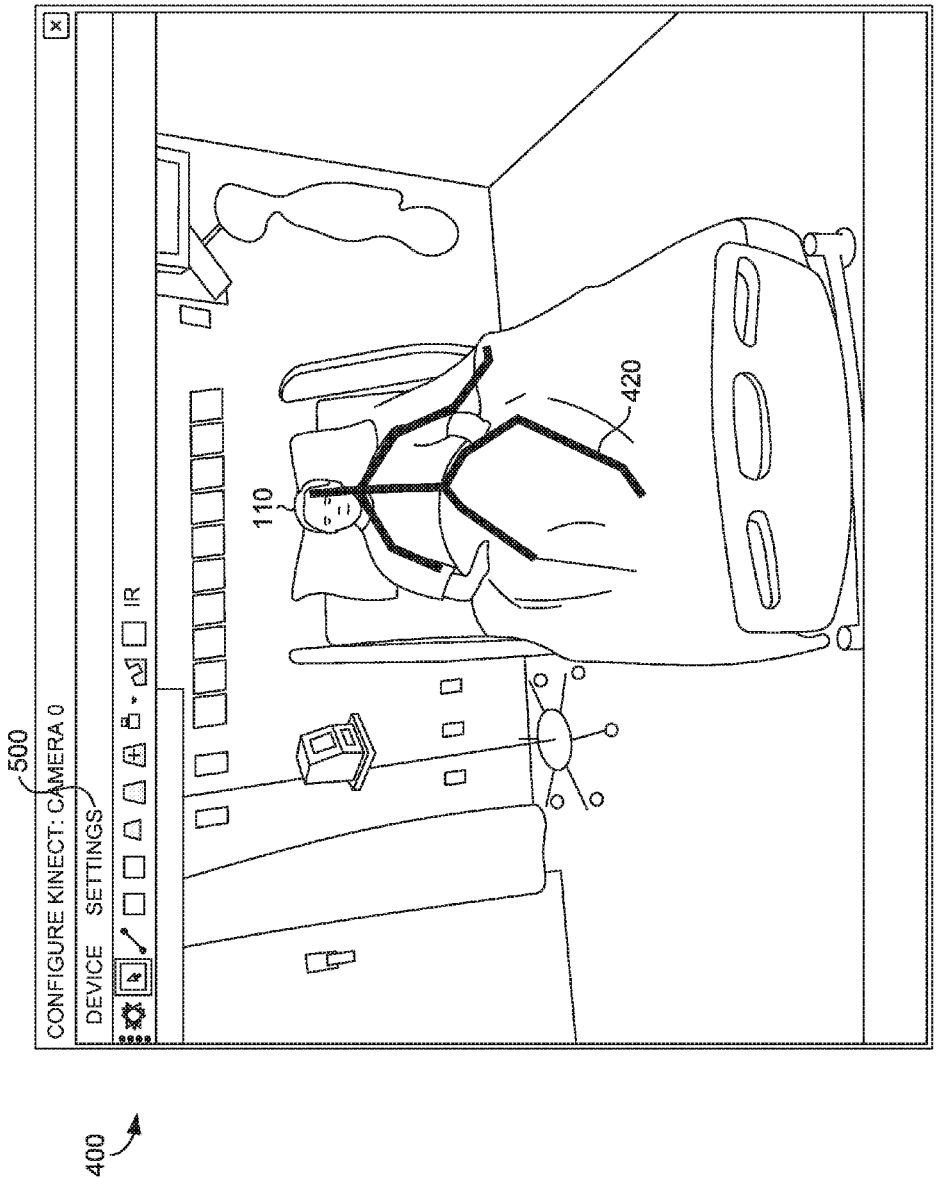
FIG. 5 is a view of an exemplary centralized monitoring primary display, in accordance with aspects of this disclosure.
Figure 6:
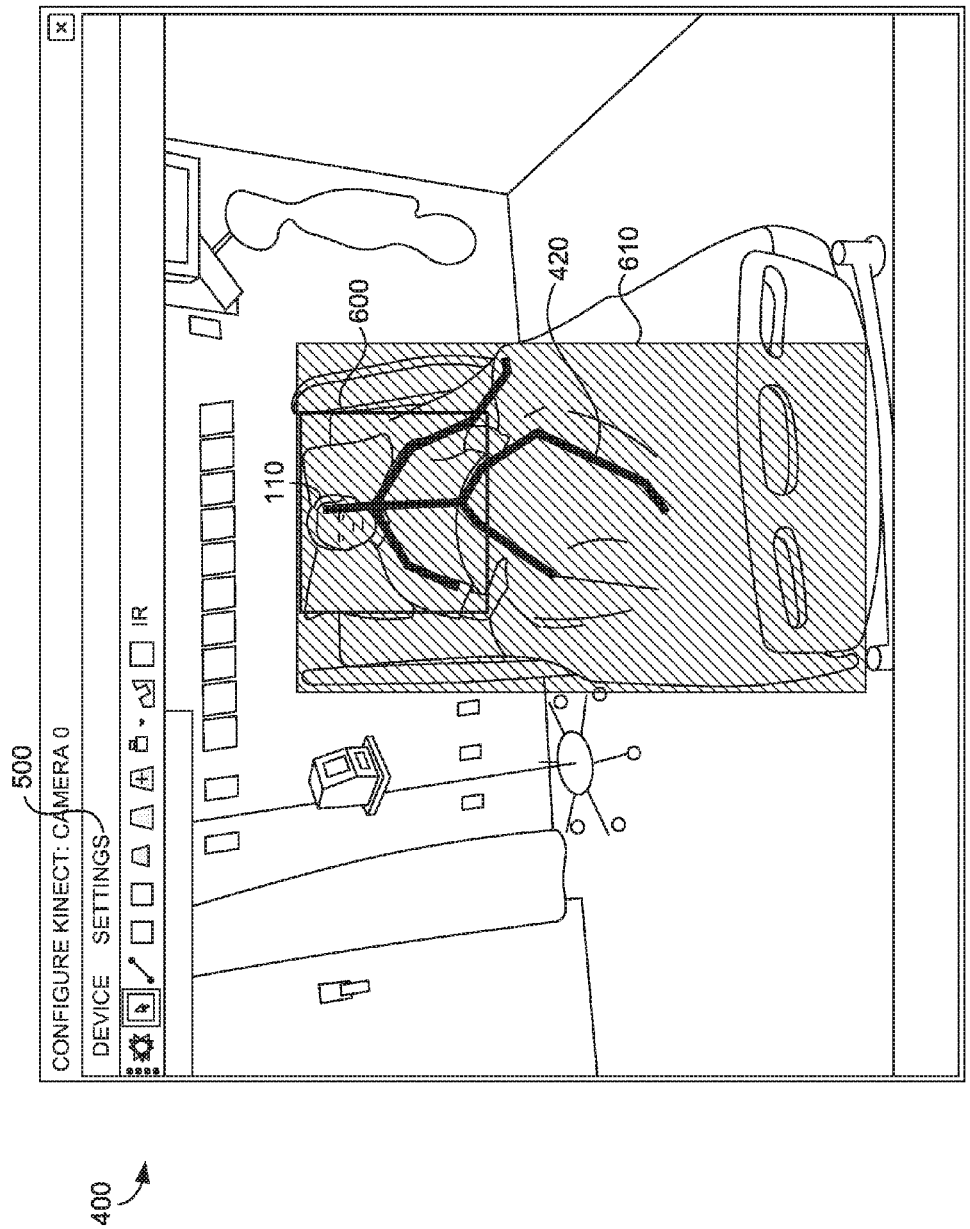
FIG. 6 is a view of an exemplary centralized monitoring primary display, in accordance with aspects of this disclosure.

FIG. 5 shows an exemplary display 400 of visual telemetry data for a single patient 110, with skeleton FIG. 420 and menu 500. FIG. 6 shows the same exemplary display 400 as FIG. 5 after a user has selected a menu option to define and/or confirm a patient zone 600 and/or a bed zone 610. The patient zone 600 and/or bed zone 610 may be automatically generated by the computerized monitoring system 130. For example, computerized monitoring system 130 may define a patient zone 600 around skeleton FIG. 420 by generating a perimeter using a default average distance from key skeleton points, such as hip or shoulder landmarks, to the perimeter of the patient zone 600. A bed zone 610 may be defined by computerized monitoring system 130, for example, by generating a perimeter using a default average distance from the perimeter of bed zone 610 to skeleton FIG. 420. Either or both of the patient zone 600 and the bed zone 610 may be used to "lock on to" the monitored individual, so that the tracking algorithms do not inadvertently shift to caregivers or visitors if different individuals' body parts cross in the camera view during interactions between the patient and others. Further, analysis of image data for position, movement, gestures, or other items of interest may be limited to the patient zone and/or the bed zone to reduce the processing capacity required to perform the analysis. If image data is transferred between remote system components, only data from the patient zone and/or the bed zone may be routinely transferred to reduce bandwidth and storage capacities required for the system's operation. In some aspects, the system may be configurable to analyze, transmit, and/or store all data within the field of view of the 3D motion sensor, either routinely or on the occurrence of a specified event, such as an alert. Although described as a "bed" zone, bed zone 610 need not be centered on a bed. A bed zone 610 may be defined based on the monitored individual's skeleton figure (e.g., with a perimeter more distant from the skeleton figure than the perimeter of patient zone 600, if a patient zone 600 is also used), or may be defined around other furniture or medical equipment supporting the monitored individual, such as a chair, chaise longue, surgical table, etc.

The patient zone 600 and/or bed zone 610 may be defined in 2 dimensions, e.g., as a perimeter around at least a portion of skeleton FIG. 420. Patient zone 600 may encompass all, or nearly all, or only a portion of the patient's body. As examples, patient zone 600 may encompass the patient's shoulders and at least part of the patient's torso, or the patient's hips to the patient's shoulders, or the patient's hips, or some or all of the patient's head to below the patient's knees. Patient zone 600 and bed zone 610 are depicted as rectangular, however, any desired shape could be used, including, without limitation, circles, squares, triangles, ovals, other regular shapes, or irregular shapes. By selecting a configuration option from menu 500, a user may alter or reset the perimeter that defines patient zone 600 and/or bed zone 610.

Figure 7:
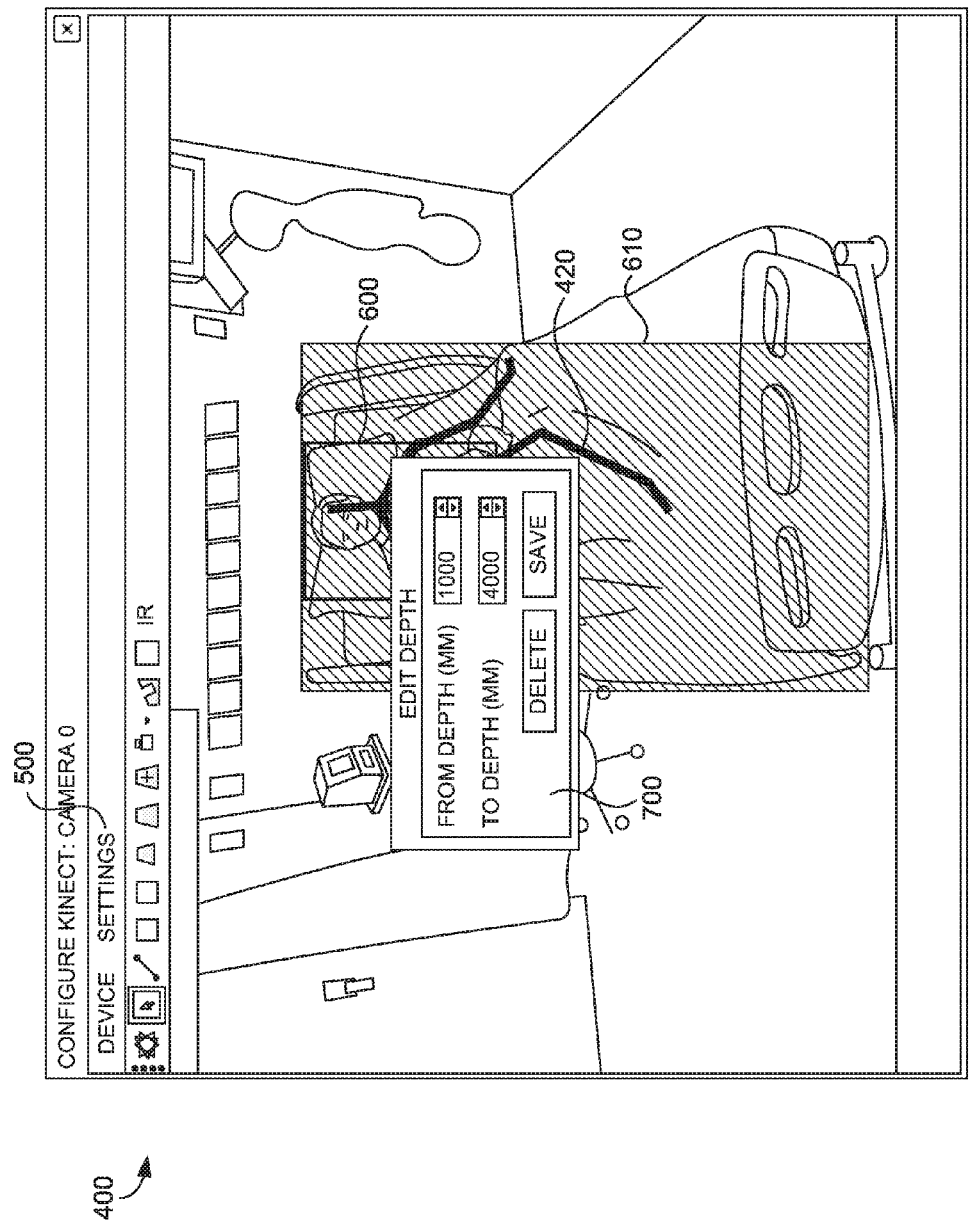
FIG. 7 is a view of an exemplary centralized monitoring primary display, in accordance with aspects of this disclosure.

As shown in FIG. 7, the patient zone 600 may have a third dimension of depth, e.g., be defined as a volume around at least a portion of skeleton FIG. 420. As with the perimeter of patient zone 600, the depth of the patient zone may be automatically generated by the computerized monitoring system 130. By selecting a configuration option from menu 500, a user may alter or reset the depth that defines patient zone 600 using a pop-up menu 700. Alternately, the perimeter and/or depth of patient zone 600 may be determined entirely by a system user, such as by entering coordinates or distances, as shown in pop-up menu 700 in FIG. 7, or by providing selection tools like drag-and-drop and pull-to-expand boxes or other shapes or tools. Patient zone 600 may be most often used around the torso of the patient. Patient zone 600 could be used around other body parts, however, the torso, including the hips and shoulders, provide a convenient limited view that can reasonably identify changes in patient position consistent with a bedsore prevention action.

Figure 8:
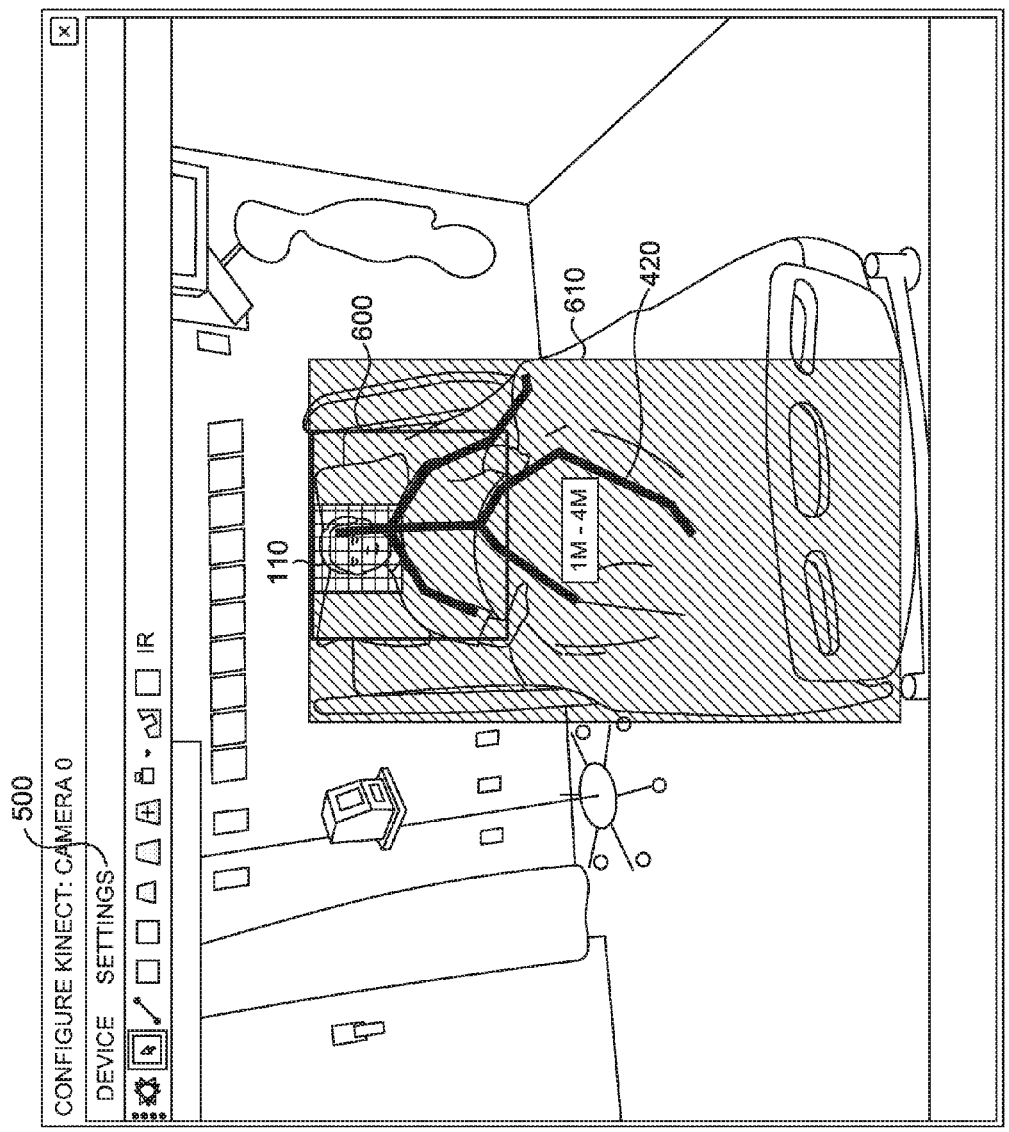
FIG. 8 is a view of an exemplary centralized monitoring primary display, in accordance with aspects of this disclosure.
Figure 9:
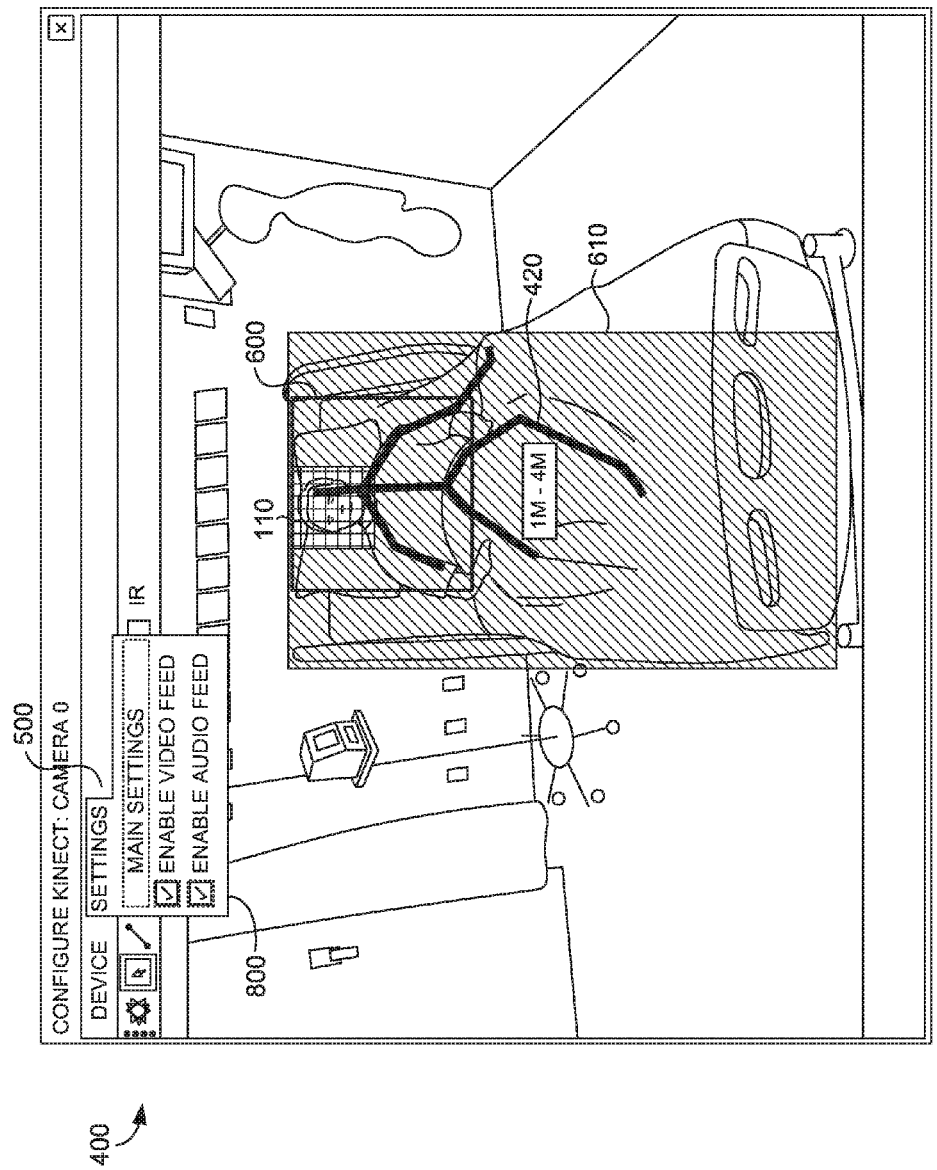
FIG. 9 is a view of an exemplary centralized monitoring primary display, in accordance with aspects of this disclosure.

FIG. 8 shows a configured patient zone 600 overlaid on visual telemetry for a monitored individual 110. FIG. 9 shows additional configuration options 800 from menu 500, allowing a user to select whether to display video telemetry ("VIDEO FEED"), audio telemetry ("AUDIO FEED"), or both.

Figure 10:
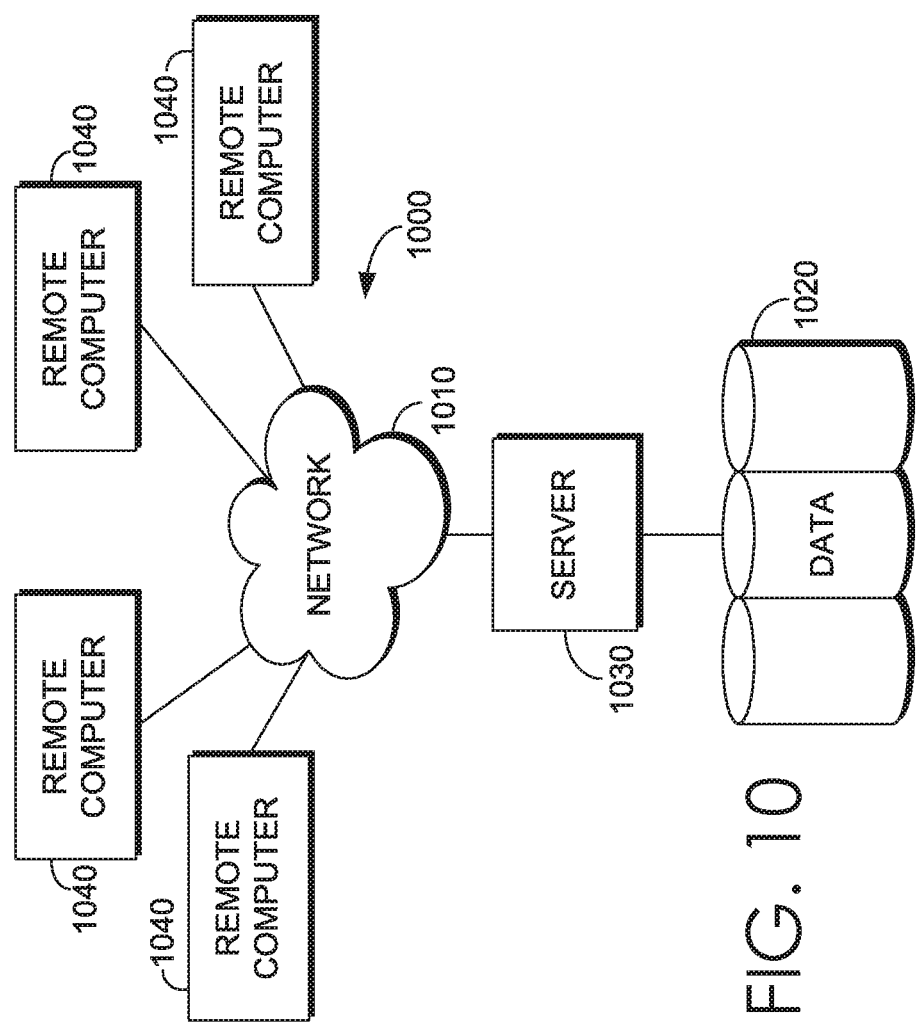
FIG. 10 is a simplified schematic view of an exemplary computing environment useful in practicing some aspects of this disclosure.

The systems, methods, and media described may be operated in an exemplary computing environment 1000 as shown in FIG. 10. Exemplary computing environment 1000 includes at least one computing device in the form of a control sever 1030. Components of control server 1030 may include, without limitation a processing unit, internal system memory, and a suitable system bus for coupling various system components, including database cluster 1020, with the control server 1030. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus.

The control server 1030 typically includes therein, or has access to, a variety of computer-readable media, for instance, database cluster 1020. Computer-readable media can be any available media that may be accessed by control server 1030, and includes volatile and nonvolatile media, as well as removable and non-removable media. By way of example, and not limitation, computer-readable media may include computer-storage media and communication media. Computer-storage media may include, without limitation, volatile and nonvolatile media, as well as removable and non-removable media implemented in any method or technology for storage of information, such as computer readable instructions, data structures, program modules, or other data. In this regard, computer-storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 1030. Computer-storage media may exclude signals per se. Computer-readable media may exclude signals per se.

Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media. The computer-storage media discussed above and illustrated in FIG. 10, including database cluster 1020, provide storage of computer readable instructions, data structures, program modules, and other data for the control server 1030.

The control server 1030 may operate in a computer network 1010 using logical connections to one or more remote computers 1040. Remote computers 1040 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices and the clinician's home or the patient's own home or over the Internet. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 1040 may also be physically located in non-traditional medical care environments so that the entire health care community may be capable of integration on the network. The remote computers 1040 may be personal computers, servers, routers, network PCs, peer devices, other common network nodes, or the like, and may include some or all of the elements described above in relation to the control server 1030. The devices can be personal digital assistants or other like devices. As described above, one or more of the remote computers 1040 may be specifically designed and/or configured to perform certain functions in relation to the systems and methods disclosed, distinguishing those devices from general purpose computers.

Exemplary computer networks 1010 may include, without limitation, local area networks (LANs) and/or wide area networks (WANs). Such networking environments are commonplace in offices, enterprise-wide computer networks, intranets, and the Internet. When utilized in a WAN networking environment, the control server 1030 may include a modem or other means for establishing communications over the WAN, such as the Internet. In a networked environment, program modules or portions thereof may be stored and/or executed on the control server 1030, in the database cluster 1020, or on any of the remote computers 1040. For example, and not by way of limitation, various application programs and/or data may reside on the memory associated with any one or more of the remote computers 1040. It will be appreciated by those of ordinary skill in the art that the network connections shown are exemplary and other means of establishing a communications link between the computers (e.g., control server 1030 and remote computers 1040) may be utilized.

In operation, a user may enter commands and information into the control server 1030 or convey the commands and information to the control server 1030 via one or more of the remote computers 1040 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 1030. In addition to a monitor, the control server 1030 and/or remote computers 1040 may include other peripheral output devices, such as speakers and a printer.

Many other internal components of the control server 1030 and the remote computers 1040 are not shown because such components and their interconnection are well known. Accordingly, additional details concerning the internal construction of the control server 1030 and the remote computers 1040 are not further disclosed herein.

Methods and systems of embodiments of the present invention may be implemented in a WINDOWS or LINUX operating system, operating in conjunction with an Internet-based delivery system. One of ordinary skill in the art will recognize that the described methods and systems can be implemented in any alternate operating system suitable for supporting the disclosed processing and communications. As contemplated, the methods and systems of embodiments of the present invention may also be implemented on a stand-alone desktop, personal computer, cellular phone, smart phone, PDA, or any other computing device used in a healthcare environment or any of a number of other locations. Nonetheless, when networked and/or programmed as described herein, the system does more than the individual, generic devices could do.

It will be appreciated by one of skill in the art that the methods disclosed may be performed by one or more computing devices executing instructions embodied on computer-readable media. The instructions may cause the one or more computers to perform the method steps disclosed when executed by one or more processors associated with the one or more computers. Such media may be embodied in hardware, firmware, computer storage media, computer-readable media, or other devices or technologies now known or later arising.

Computer-readable media embodying one or more computer executable instructions may include a data acquisition module. The data acquisition module may acquire data from one or more 3D motion sensors 120, from a wireless transmitter 310, or from a wireless receiver 320. The data acquisition module may receive data sent to it by one or more devices, or may request or retrieve data from one or more devices. The data acquisition module may further acquire data from one or more databases and/or electronic files available to the system, such as an EHR system, a database containing photographs or other identifiers for patients and/or caregivers, or any other system or file containing information useful in determining whether a caregiver has taken measures to prevent patient bedsores.

A virtual zone module may define and/or provide a user interface for defining, altering, and/or confirming a virtual patient zone and/or a virtual bed zone. The virtual zone module may use the virtual patient zone and/or virtual bed zone to create one or more subsets of data acquired by the data acquisition module. For example, a subset of data limited from the entire field of view of a 3D motion sensor may be generated for only data from within a virtual patient zone or a virtual bed zone. Analysis of the data may be limited to the subset of data, so as to conserve processing capacity in the system by not analyzing data from portions of the field of view that are unlikely to be relevant to whether or not a bedsore prevention action has been completed. Similarly, subsets of data may be defined for communication and/or storage purposes, to conserve communications bandwidth and/or storage capacity requirements for the system.

An action determination module may be configured to analyze data acquired by the data acquisition module, and/or subsets of data acquired by the data acquisition module. The action determination module may use image analysis and/or the strength of a signal between a wireless receiver and a transmitter to infer the distance between a caregiver and a patient, and determine whether the caregiver is close enough to the patient to possibly perform a bedsore prevention action. The action determination module may comprise one or more timers, or may comprise a clock, or both, for monitoring and/or calculating intervals between bedsore prevention actions and/or the duration of a caregiver's contact with a patient. The action determination module may communicate alerts regarding incomplete bedsore prevention actions and/or confirmations of completed bedsore prevention actions, e.g., to a computerized communication system, a centralized monitoring station, and/or a database.

A communication module may be configured to receive alerts and/or confirmations from the action determination module, and to select and transmit an appropriate message to a patient, a caregiver, an alternate caregiver, other human users, a centralized monitoring station, and/or others. The communication module may select a mode of communication, e.g., an automated phone call, an e-mail, a text display in a patient's room, etc., based on user preferences, default settings, and/or the nature of the message to be communicated. The communication module may select a message based on the nature of the communication (e.g., whether the caregiver did not approach a patient for a scheduled bedsore prevention action, the caregiver did not remain within proximity to the patient long enough to complete a bedsore prevention action, the patient has self-repositioned or is capable of self-repositioning, the completion of the bedsore prevention action is being confirmed, etc.), and may further select a language for delivering the message. Different modes of communication, different message content and/or different languages may be selected for different alert recipients, or the same alert or confirmation may be sent to all recipients, using the same or different modes of communication for different recipients, if there is more than one recipient.

A central monitoring module may aggregate data from the monitoring of multiple patients. Image data and/or video, if available, may be displayed on a primary display, rendered as human-intelligible images. Signal strength data, if available, may be displayed on a primary display, and may be presented as a measurement or as a graphical representation or both. The primary display of signal strength data may include an indication of one or more threshold levels for signal strength, such as when the signal strength is sufficient to infer that the caregiver is in the room with the patient, and/or when the signal strength is sufficient to infer that the caregiver is in physical contact with the patient and/or close enough to perform a bedsore prevention action. The central monitoring module may move a display of data related to a patient to an alert display, or duplicate a display of data related to a patient on an alert display, upon receiving an alert for that patient. The central monitoring module may move a display of data related to a patient to a primary display, or may remove a display of data related to a patient from an alert display, after receiving a response to an alert and/or confirmation that a bedsore prevention action has been completed for that patient. The central monitoring module may be configured to permit a human attendant using the central monitoring module to access the communication module to send a message to one or more recipients regarding an alert, a response to an alert, a lack of response to an alert, and/or confirmation of completion of a bedsore prevention action. Messages sent via the central monitoring module may be pre-recorded or pre-determined (e.g., selected from a menu of available messages) or may be recorded, typed, or otherwise entered by the human attendant via the central monitoring module and communication module.

A recordation module may store data related to alerts and/or confirmations, including any received response (e.g., a response entered into the system by a human user), observed response, or the apparent lack of a response to any alert. The data may be stored in a database associated with the system, or in any other desired electronic file or storage location. In some embodiments, the recordation module may store data for a particular patient in an EHR, case report form, or other medical recordkeeping file. In some embodiments, the recordation module may store data in a database or file accessible to an EHR system and/or other systems. In some embodiments, the recordation module may store all data acquired for a particular patient, or only data regarding alerts and/or confirmations, or only data for a designated timeframe.

All steps and flowcharts described herein, including in the attached figures, are meant to be illustrative. It should be understood that other steps may be used with the illustrated steps, and, further, that some steps may be useful without the practice of other steps included in the figures. The illustrated sequence of steps is also exemplary, and, unless described otherwise, the steps may be performed in different sequences, combinations, and/or subcombinations.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

What is claimed is:

1. A method of reducing the chance that a patient will develop a bedsore, the method performed by one or more processors of a computerized monitoring system and comprising:
    receiving, from a wireless receiver associated with one of a caregiver and a patient, data indicating a signal strength for a signal received from a wireless transmitter associated with the other of the caregiver and the patient, wherein the wireless receiver associated with one of the caregiver and the patient is worn or carried by one of the caregiver and the patient and wherein the wireless transmitter associated with the other of the caregiver and the patient is worn or carried by the other of the caregiver and the patient;
    determining whether the signal strength is above a threshold signal strength;
    determining whether one or more bedsore prevention actions have been performed at least by determining whether the signal strength remains over the threshold signal strength for at least a predetermined period of time; and
    electronically communicating a determination of whether one or more bedsore prevention actions have been performed.

2. The method of claim 1, wherein when the signal strength has not remained over the threshold signal strength for at least the predetermined period of time, electronically communicating the determination comprises notifying a computerized communication system in electronic communication with the computerized monitoring system that the caregiver has not performed one or more bedsore prevention actions.

3. The method of claim 2, wherein the computerized communication system issues an alert directed to the patient, the caregiver, an alternate caregiver, a centralized monitoring station, or a combination thereof.

4. The method of claim 1, further comprising receiving data from a 3D motion sensor co-located with the patient.

5. The method of claim 4, further comprising determining, based on the data from the 3D motion sensor, whether the patient has changed position consistent with a bedsore prevention action within a specified time interval.

6. The method of claim 5, further comprising electronically communicating to a computerized communication system in electronic communication with the computerized monitoring system that the patient has not sufficiently changed position to comply with a bedsore prevention action within the specified time interval and wherein the computerized communication system issues an alert.

7. The method of claim 6, wherein the alert is directed to the patient, the caregiver, an alternate caregiver, a centralized monitoring station, or a combination thereof.

8. The method of claim 4, wherein images from the 3D motion sensor are displayed on a centralized monitoring station primary display.

9. The method of claim 1, wherein the wireless transmitter is associated with the caregiver and the method further comprises identifying the caregiver based on data received from the wireless transmitter.

10. The method of claim 9, further comprising receiving data from a 3D motion sensor co-located with the patient, and using the data from the 3D motion sensor to confirm the identity of the caregiver.

11. The method of claim 1, further comprising recording in a database the determination of whether one or more bedsore prevention actions have been performed.

12. A system for reducing the chance that a patient will develop a bedsore, the system comprising:
    a wireless transmitter configured to be worn or carried by one of a caregiver and a patient;
    a wireless receiver configured to be worn or carried by the other of the caregiver and the patient, the wireless receiver configured to receive transmissions from the wireless transmitter when the wireless transmitter is within range of the wireless receiver;
    a computerized monitoring system configured to:
        receive signal strength data from the wireless receiver, wherein signal strength data indicates a strength of a signal of the wireless transmitter received by the wireless receiver when the wireless receiver is within range of the wireless transmitter;
        determine whether the signal strength is above a threshold signal strength; and
        determine whether one or more bedsore prevention actions have been performed at least by determining whether the signal strength remains over the threshold signal strength for at least a predetermined period of time; and
    a computerized communication system configured to:
        receive an alert from the computerized monitoring system upon a determination that one or more bedsore prevention actions have been performed; and
        communicate an alert to at least one of the patient, the caregiver, an alternate caregiver, a database, and a centralized monitoring station.

13. The system of claim 12, further comprising a 3D motion sensor, wherein the computerized monitoring system is configured to receive image data from the 3D motion sensor.

14. The system of claim 13, wherein the centralized monitoring station comprises a primary display, and image data from the 3D motion sensor is sent to the centralized monitoring station and displayed on the primary display.

15. The system of claim 13, wherein the computerized monitoring system is further configured to determine, using data from the 3D motion sensor, whether the patient has changed position consistent with a bedsore prevention action within a specified time interval for performing the bedsore prevention action.

16. The system of claim 15, wherein the computerized communication system sends a confirmation notification to the caregiver when the patient has changed position consistent with a bedsore prevention action.

17. The system of claim 15, wherein the computerized monitoring system is configured to determine whether the patient has changed position consistent with a bedsore prevention action within the specified time interval for performing the bedsore prevention action after determining that the signal strength remains over the threshold signal strength for at least the predetermined period of time during the specified time interval.

18. Computer storage media, excluding signals per se, embodying computer-executable instructions for performing a method for reducing the chance that a patient will develop a bedsore, the method comprising:

receiving data from a wireless receiver that is worn or carried by one of a caregiver and a patient, wherein the data received from the wireless receiver indicates a signal strength for a signal received by the wireless receiver from a wireless transmitter that is worn or carried by the other of the caregiver and the patient;

analyzing data from the wireless receiver to determine whether one or more bedsore prevention actions have been performed at least by determining whether the signal strength remains over a threshold signal strength for at least a predetermined period of time during a specified time interval; and sending one or more alerts upon determining that one or more bedsore prevention actions have not been performed.

19. The method of claim 1, wherein determining whether the caregiver has performed one or more bedsore prevention actions comprises determining whether the signal strength remains over the threshold signal strength for at least the predetermined period of time during a specified time interval.

20. The method of claim 19, wherein when it is determined that the signal strength remains over the threshold signal strength for at least the predetermined period of time during the specified time interval, a new time interval beings for monitoring whether the one or more bedsore prevention actions have been performed.

* * * * *

UNITED STATES PATENT AND TRADEMARK OFFICE
CERTIFICATE OF CORRECTION

| | |
|---|---|
| PATENT NO. | : 10,342,478 B2 |
| APPLICATION NO. | : 15/148151 |
| DATED | : July 9, 2019 |
| INVENTOR(S) | : Neil Kusens |

It is certified that error appears in the above-identified patent and that said Letters Patent is hereby corrected as shown below:

On the Title Page

Page 3, Column 02, Other Publications, Line 21: Please remove "Notice Notice" and replace with --Notice--.

In the Specification

Column 15, Line 28: Please remove "FIGS." and replace with --figures.--.

Column 15, Line 40: Please remove "FIG. 420" and replace with --figure 420--.

Column 15, Line 47: Please remove "FIG. 420" and replace with --figure 420--.

Column 15, Lines 53-54: Please remove "FIG. 420." and replace with --figure 420.--.

Column 16, Line 14: Please remove "FIG. 420." and replace with --figure 420.--.

Column 16, Line 29: Please remove "FIG. 420." and replace with --figure 420.--.

In the Claims

Column 23, Line 25: Please remove "beings" and replace with --begins--.

Signed and Sealed this
Twenty-seventh Day of August, 2019

Andrei Iancu
*Director of the United States Patent and Trademark Office*